United States Patent [19]
Chubbuck

[11] Patent Number: 6,113,553
[45] Date of Patent: Sep. 5, 2000

[54] TELEMETRIC INTRACRANIAL PRESSURE MONITORING SYSTEM

[75] Inventor: John G. Chubbuck, Noble, Okla.

[73] Assignee: LifeSensors, Inc., Noble, Okla.

[21] Appl. No.: 09/136,667

[22] Filed: Aug. 18, 1998

Related U.S. Application Data

[63] Continuation of application No. 08/611,547, Mar. 5, 1996, abandoned.

[51] Int. Cl.$^7$ .................................................. A61B 8/00
[52] U.S. Cl. ........................................ 600/561; 73/729.1
[58] Field of Search ........................... 600/561; 73/718, 73/722, 724, 728, 729.1

[56] References Cited

U.S. PATENT DOCUMENTS

| | | | |
|---|---|---|---|
| 3,027,769 | 4/1962 | Coon | 73/398 |
| 3,356,963 | 12/1967 | Buck | 331/65 |
| 3,405,559 | 10/1968 | Moffatt | 73/398 |
| 3,422,324 | 1/1969 | Webb | 317/246 |
| 3,453,546 | 7/1969 | Fryer | 325/143 |
| 3,625,199 | 12/1971 | Summers | 128/2 |
| 3,757,770 | 9/1973 | Brayshaw et al. | 128/2 |
| 3,838,684 | 10/1974 | Manuel et al. | 128/2.05 |
| 3,886,948 | 6/1975 | Hakim | 128/350 |
| 3,911,902 | 10/1975 | Delpy | 128/2.05 |
| 3,924,635 | 12/1975 | Hakim | 128/350 |
| 3,926,705 | 12/1975 | Todd | 156/155 |
| 3,958,558 | 5/1976 | Dunphy et al. | 128/2 |
| 3,977,391 | 8/1976 | Fleischmann | 128/2 |
| 4,006,735 | 2/1977 | Hittman et al. | 128/2 |
| 4,026,276 | 5/1977 | Chubbuck | 128/2 |
| 4,062,354 | 12/1977 | Taylor et al. | 128/2 |
| 4,096,758 | 6/1978 | Moore | 73/718 |
| 4,109,535 | 8/1978 | Reed et al. | 73/706 |
| 4,114,606 | 9/1978 | Seylar | 128/2.05 |
| 4,124,023 | 11/1978 | Fleischmann et al. | 128/2 |
| 4,127,110 | 11/1978 | Bullara | 128/2 |
| 4,127,449 | 11/1978 | LeRoy et al. | 128/654 |
| 4,157,094 | 6/1979 | Patel | 128/349 |
| 4,186,749 | 2/1980 | Fryer | 128/748 |
| 4,206,762 | 6/1980 | Cosman | 128/660 |
| 4,265,252 | 5/1981 | Chubbuck et al. | 128/748 |
| 4,281,666 | 8/1981 | Cosman | 128/748 |
| 4,354,506 | 10/1982 | Sakaguchi et al. | 128/748 |
| 4,378,809 | 4/1983 | Cosman | 128/748 |
| 4,471,786 | 9/1984 | Inagaki et al. | 128/748 |
| 4,519,401 | 5/1985 | Ko et al. | 118/748 |
| 4,593,703 | 6/1986 | Cosman | 128/748 |
| 4,653,508 | 3/1987 | Cosman | 128/748 |
| 4,676,255 | 6/1987 | Cosman | 128/748 |
| 4,835,636 | 5/1989 | Cosman | 128/748 |
| 5,673,703 | 10/1997 | Fisher et al. | 128/739 |
| 5,704,352 | 1/1998 | Tremblay et al. | 128/630 |

OTHER PUBLICATIONS

Comparison of Telemetric Epidural and Intraventricular Pressures (2 pages, date unknown).
Continuous Recording of ICP in the Normal Monkey, Reprint from *Intracranial Pressure IV,* ®Springer–Verlag Berlin Heidelberg 1980 (5 pages).
Intracranial pressure in the normal monkey while awake and asleep, *J. Neurosurg.,* vol. 51, Aug. 1979 (5 pages).
Ten–Year Follow–up on the Performance of a Telemetric Intracranial Pressure Sensor, *Neurosurgery,* vol. 22, No. 5, ®1988 (4 pages).

(List continued on next page.)

*Primary Examiner*—Francis J. Jaworski
*Attorney, Agent, or Firm*—Dunlap, Codding & Rogers

[57] ABSTRACT

The present invention relates to an apparatus for monitoring the intracranial pressure of a patient. The apparatus includes an implantable sensor implanted in the skull of a patient. The implantable sensor senses pressure and outputs a signal indicative of the pressure in the patient's skull. The apparatus further includes a probe receiving the signal output by the implantable sensor when the probe is positioned near the implantable sensor. The probe outputs a signal indicative of the pressure sensed by the implantable sensor. An interrogation circuit is provided for receiving the signal output by the probe and automatically outputting a digital signal proportional to the pressure sensed by the implantable sensor.

34 Claims, 11 Drawing Sheets

OTHER PUBLICATIONS

Continuous Intracranial Pressure Recording in Adult Hydrocephalus, *Surgical Neurology*, vol. 13, May 1980 (6 pages).

Long–term intracranial pressure recording in the management of pseudotumor cerebri, *J. Neurosurg.*, vol. 49, Aug. 1978 (13 pages).

The Radionics ICP Tele–Monitor System, Radionics, Inc., ®1985 (16 pages).

Radionics Offers New Advances in RF Neurosurgery, Radionics, Inc., (1 page, date unknown).

Radionics Neurosurgical Instruments, Product Information Tele–Shunt System, Radionics, Inc., ®1984 (7 pages).

Radionics Neurosurgical Instruments, Product Information Standard Shunt Valve System, Radionics, Inc. (2 pages, date unknown).

The Radionics Shunt Valve System, Simple in design, reliable in performance, Radionics, Inc., (7 pages, date unknown).

Telemetric ICP monitoring after surgery for posterior fossa and third ventricular tumors, *J. Neurosurg.*, vol. 60, Mar. 1984 (3 pages).

The Relationship between Ventricular Fluid Pressure and Body Position in Normal Subjects and Subjects with Shunts: A Telemetric Study, *Neurosurgery*, vol. 26, No. 2, ®1990 (4 pages).

A Telemetric Pressure Sensor for Ventricular Shunt Systems, *Surgical Neurology*, vol. 11, Apr. 1979 (3 pages).

Telemetric ICP Measurement in Normal and Shunted, Hydrocephalic Patients, *Concepts Pediatric Neurosurgery*, vol. 6, Karger, Basel 1985 (10 pages).

Radio Telemetry for the Measurement of Intracranial Pressure, *J. Neurosurgery*, vol. 27 #5, 1967, pp. 428–432.

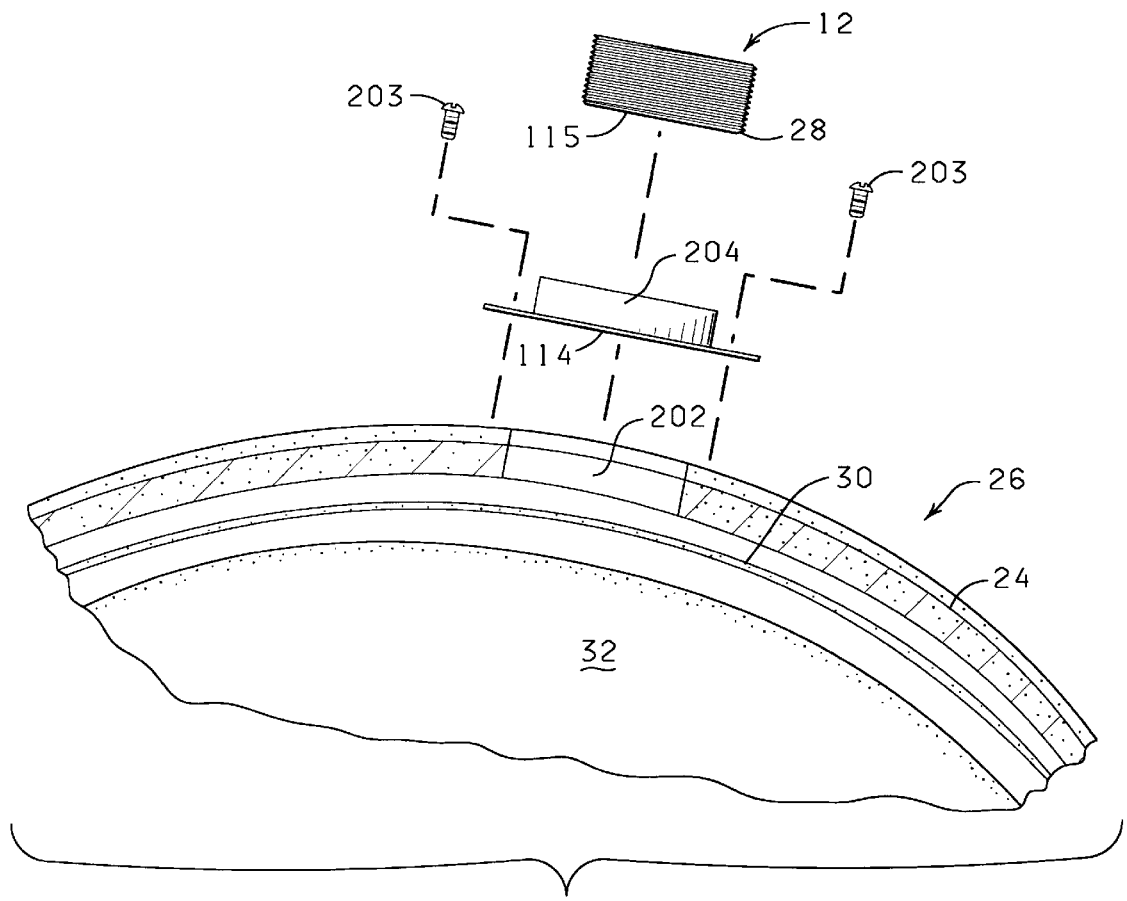
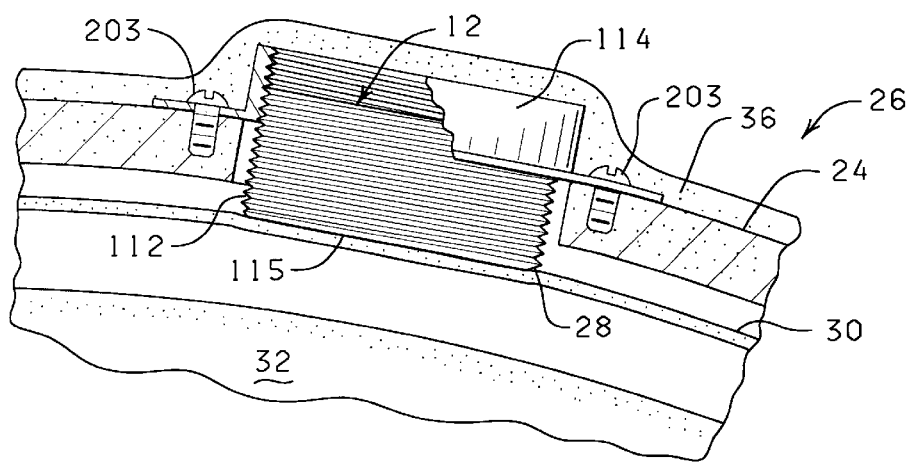

TELEMETRIC INTRACRANIAL PRESSURE MONITORING SYSTEM

This is a continuation of application Ser. No. 08/611,547 filed on Mar. 5, 1996, and now abandoned which disclosure is hereby incorporated herein by reference.

BACKGROUND OF THE INVENTION

1. Field of the Invention

The present invention relates to apparatus and methods for monitoring the pressure within a cavity in a patient, and more specifically, but not by way of limitation, to devices and methods for telemetrically monitoring the intracranial pressure of a patient.

2. Description of Related Art

The need for monitoring intracranial pressure in patients has long been recognized. Elevated intracranial pressure may be tolerated for only a few hours or perhaps as long as days or weeks. In all circumstances, unmonitored and uncontrolled elevated intracranial pressure will eventually lead to cerebral injury and can lead to visual loss or to cerebral white matter injury and dementia.

The general pathophysiological process that can elevate intracranial pressure regardless of the specific disease includes brain tumors, pseudotumor cerebri, hydrocephalus, severe head trauma and other situations where patients are subject to brain swelling, edema, obstruction of cerebral spinal fluid pathways or intracranial space occupying lesions. Convenient and accurate monitoring of the intracranial pressure in these situations frequently allows correctional emergency procedures when intracranial pressure rises or falls to dangerous levels.

Currently available methods for monitoring intracranial pressure involve measuring cerebral spinal fluid pressure via a lumbar puncture as well as more directly measuring pressure using a catheter passing through the skull and the scalp to some data acquisition system exterior to the patient. In some cases, the catheter is simply a plastic tube which vents the subarachnoid pressure to an electronic readout pressure gauge. A more recently developed class of sensors involve a microminiature pressure transducer located in the distal end of the catheter. The catheter is passed through the brain tissue placing the pressure transducer into one of the ventricles. A fiberoptic filament communicates the measured pressure data to the external data acquisition portion of the system.

Such catheter type systems are generally unsatisfactory for long term monitoring of intracranial pressure because of the inherent dangers of: infection; patient discomfort; reduced patient mobility; and surgical procedures necessary to remove the pressure transducer when it is no longer needed.

Long term intracranial pressure monitoring without undue risk of these dangers requires a totally implantable sensor that dan survive structurally and provide a measurable and meaningful response to intracranial pressure for extended periods of time. In the 1970's and early 1980's, the Applied Physics Laboratory of John Hopkins University (JHU/APL), under the direction of Applicant, designed and developed a telemetric intracranial pressure monitoring system. The telemetric intracranial pressure monitoring system developed by JHU/APL comprised a sensor which was implanted into a burr hole in the skull wall; and a telemetric data acquisition system which eliminated the need for a wire or catheter coupling as the method of communication between the sensor and the data acquisition system.

The sensor that was developed by JHU/APL is disclosed in U.S. Pat. No. 4,265,252, issued to Chubbuck et al. on May 5, 1981. The sensor comprises a passive device consisting of a RF resonant circuit having a resonant frequency varying from about 50 MHz to about 100 MHz.

The telemetric data acquisition system developed by JHU/APL is disclosed in U.S. Pat. No. 4,114,606, issued to Seylar on Sep. 19, 1978. The Seylar patent discloses a data acquisition system comprising a high frequency sweeping signal generator with crystal markers. The sweeping signal generator would drive an interrogation coil through a 50 ohm coaxial cable. The interrogation coil was placed externally of a patient's skull but close to the sensor so that a signal showing the frequency at which the sensor resonated was displayed on an X-Y display oscilloscope. Medical personnel would then convert the signal displayed on the X-Y display oscilloscope to the actual intracranial pressure by way of referring to calibration charts and barometric correction charts.

The telemetric intracranial pressure monitoring system developed by JHU/APL was developed and tested from about 1976 through about 1983. During this time, 127 implantable sensors were implanted in human patients. The results of these studies were reported in journals from about 1979 through about 1988 and typical articles are "Continuous Intracranial Pressure Recording in Adult Hydrocephalus", written by G. Gucer, L. J. Viernstein and A. E. Walker, *Surg. Neurol.* 13:5, May 1980; and "Ten-Year Follow-up on the Performance of a Telemetric Intracranial Pressure Sensor", written by G. Gucer, L. J. Viernstein, A. Wang and R. Szymanski, *Neurosurgery* 22:5 1988.

The results of these studies verified that the sensor of the telemetric intracranial pressure monitoring system reliably produced an intracranial pressure measurement. However, the zero pressure resonant frequency of the sensor (or calibrated baseline) changed or drifted not due to actual intracranial pressure changes. More specifically, the zero pressure reading of the implantable sensor increased $1.0 \pm 0.2$ mm $H_2O$/day (0.074 mm Hg/day) over a period of $6.8 \pm 1.6$ years.

Furthermore, it was found that a subgroup of implantable sensors displayed a decreasing zero pressure reading not due to actual intracranial pressure decreases. The decreasing zero pressure reading was found to be caused by seepage of body fluids into the implantable sensor.

It was reported during the study that only some of the nurses involved in the study were able to make the conversion from the resonant frequency of the implantable sensor to the intracranial pressure of the patient. It was ultimately concluded that: the bulk of the laboratory test equipment used to read the implantable sensor was inconsistent with space allocation requirements of intensive care units; the technical expertise required to operate the test equipment was not likely to be found among intensive care personnel; and reference to calibration and correction charts complicated the data acquisition system's use by medical personnel.

The increasing and decreasing of the sensor's zero pressure reading is commonly referred to in the art as "baseline drift" because the zero pressure reading of the implantable sensor drifts away from a calibration baseline not due to actual intracranial pressure changes.

Based on these experiences, the systems disclosed in the Chubbuck and Seylar patents were not as suitable as is desired to be utilized in the hospital environment.

Thus, a need exists for an improved telemetric intracranial pressure monitoring system for the long term continuous or intermittent monitoring of a patient's intracranial pressure. However, such an improved telemetric intracranial pressure monitoring system must also be cost efficient and substantially maintenance-free. It is to such an improved telemetric intracranial pressure monitoring system that the present invention is directed.

BRIEF DESCRIPTION OF THE DRAWINGS

FIG. 6 is a schematic view illustrating the manner in which the implantable sensor is mounted in the skull of a patient.

FIG. 7 is a fragmental, cross-sectional view of the implantable sensor implanted within the skull of a patient.

DETAILED DESCRIPTION

Figure 1:
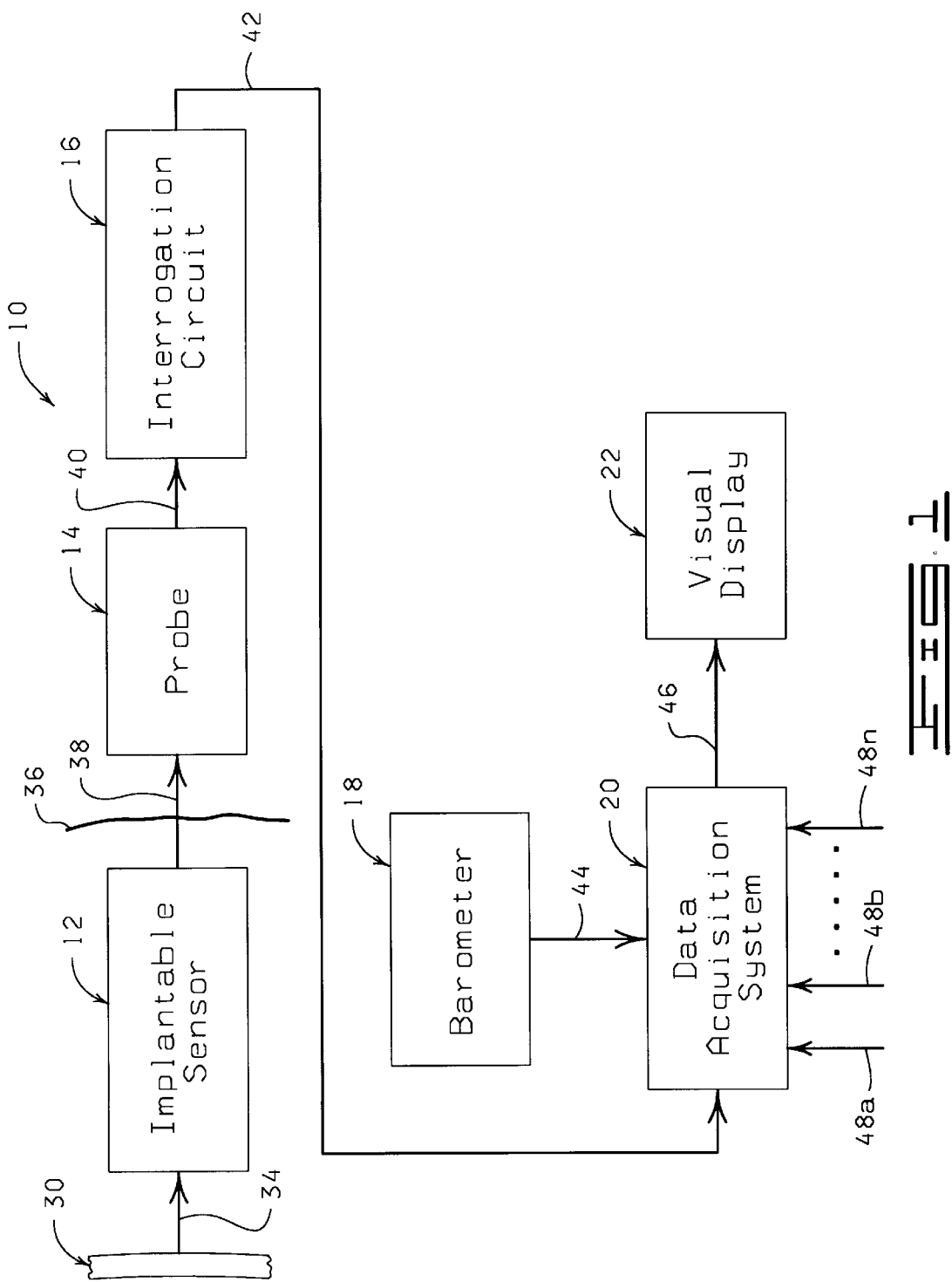
FIG. 1 is a signal flow diagram of a telemetric intracranial pressure monitoring system constructed in accordance with the present invention.

Shown in FIG. 1 is an improved telemetric intracranial pressure monitoring system 10 for the long term continuous or intermittent monitoring of the pressure within the cranium of a patient. As diagrammatically shown in FIG. 1, the improved telemetric intracranial pressure monitoring system 10 basically comprises an implantable sensor 12, a probe 14, an interrogation circuit 16, a barometer 18, a data acquisition system 20 and a visual display 22.

The implantable sensor 12 is adapted to be mounted within the skull 24 (FIGS. 6 and 7) of a patient 26 whose intracranial pressure is to be monitored. When implanted, a lower end 28 (FIG. 7) of the implantable sensor 12 is typically positioned against the dura 30 (FIGS. 1, 6 and 7), a membrane interposed between the skull 24 and the brain 32 of the patient 26. The implantable sensor 12 epidurally senses subdural (cranial) pressure of the patient 26 as indicated by signal path 34 in FIG. 1. The implantable sensor 12 compares the cranial pressure to a pressure reference contained within the implantable sensor 12 and outputs a pressure signal indicative of the deviation of cranial pressure from the pressure reference over a signal path 38.

When the probe 14 is located externally of the scalp 36 of the patient 26 and near the implantable sensor 12, the sensor output signal is received by the probe 14 from the implantable sensor 12 via the signal path 38. In response thereto, the probe 14 outputs a probe output signal indicative of the cranial pressure of the patient 26 over a signal path 40 to be received by the interrogation circuit 16. Typically, the interrogation circuit 16 transmits RF input signals to the probe 14 via signal path 40 and simultaneously receives DC output signals indicative of the cranial pressure of the patient 26 output by the probe 14 via such signal path 40. The signal path 40 can be air way transmission, cable transmission or any other suitable transmission link.

The interrogation circuit 16 receives the probe output signal transmitted from the probe 14 over signal path 40 and in response thereto converts such probe output signal into a format perceivable by the data acquisition system 20. The interrogation circuit 16 is typically adapted to convert the probe output signal transmitted by the probe 14 into either a digital or analog format proportional to the cranial pressure of the patient 26 as sensed by the implantable sensor 12. As will be understood by those skilled in the art, the interrogation circuit 16 may convert the probe output signal into a digital signal proportional to the cranial pressure of the patient 26, and then convert such digital signal into an analog signal by way of a Digital to Analog converter (D/A converter), for example if an analog signal is desired. Once converted, the signal is output by the interrogation circuit 16 over a signal path 42. The signal path 42 can be a cable and/or an air way transmission and/or a computer bus or any other suitable transmission link.

The data acquisition system 20 receives the signal output by the interrogation circuit 16 via signal path 42, and also receives a signal via signal path 44 from the barometer 18 indicative of atmospheric pressure. In response thereto, the data acquisition system 20 automatically computes the intracranial pressure within the skull 24 of the patient 26 and generates a signal indicative of such intracranial pressure. The signal generated by the data acquisition system 20 can then be transmitted over signal path 46 to be received by the visual display 22 operably connected to the data acquisition system 20 for displaying such signal. Alternatively, the signal can be stored on magnetic, optical or solid state media and subsequently transmitted over signal path 46 to be displayed by the visual display 22.

The visual display 22 can be remotely and/or locally connected to the data acquisition system 20. For example, the data acquisition system 20 can be connected to an ICU monitoring system (not shown) located near the patient 26 for remotely displaying the intracranial pressure of the patient 26. Or, the data acquisition system 20 can be directly connected to a monitor for locally displaying the intracranial pressure of the patient 26.

The data acquisition system 20 further includes a plurality of inputs 48a–48n for automatically receiving data from sensors (not shown) sensing various physiological data relating to the patient 26, such as heart rate, blood pressure, respiratory rate, arterial oxygen saturation, end-tidal $CO_2$ concentration, temperature and the like via a plurality of signal paths. The sensors can be conventional sensors and the signal paths can be any suitable transmission link, such as cable transmissions, air way transmissions or the like. Furthermore, the data can be collected by retrieving output (typically analog output) from a patient's ICU monitoring system. Once received, the data may be displayed and stored independently of the intracranial pressure of the patient 26.

The data acquisition system 20 can be a conventional personal computer system, such as the type manufactured by IBM or Compaq, running a custom program as is customary in the art. The custom program may be written by BME Systems, Inc. located at 2340 Monumental Ave., Baltimore, Md. 21227. The barometer 18 can be a Model EIS/1250-01, obtainable from Sensotec of Columbus, Ohio, for example.

In general, the telemetric intracranial pressure monitoring system 10 of the present invention is constructed to monitor the intracranial pressure of the patient 26 and to provide output indications which are indicative of such intracranial pressure that are readily understandable by care providers without the need for manual conversion. Thus, a care provider can view intracranial pressure immediately in units of millimeters of mercury or centimeters of water and render care to the patient 26 immediately.

Figure 2:
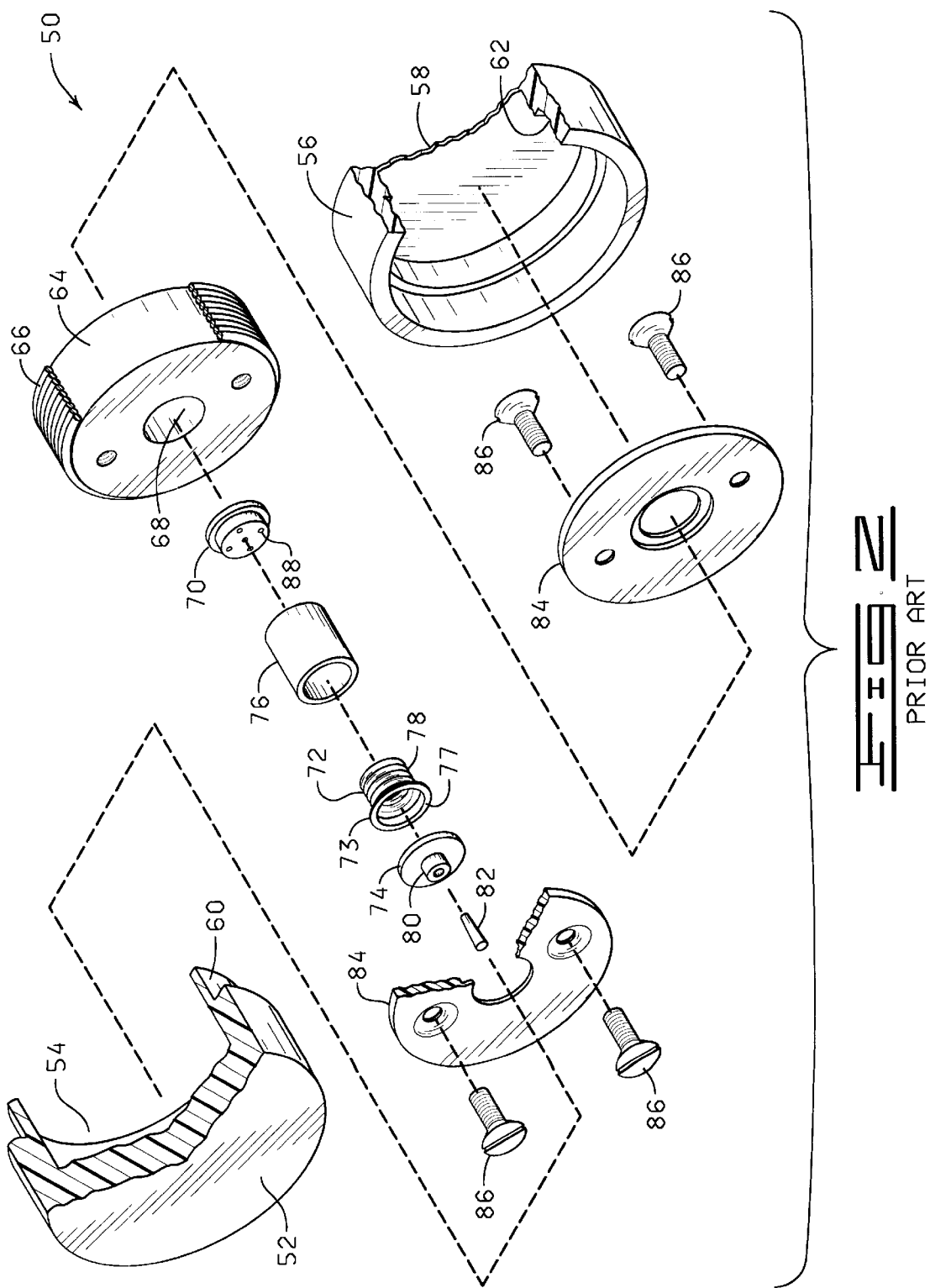
FIG. 2 is an exploded, perspective assembly view of a prior art intracranial pressure sensor.

Shown in FIG. 2 is a typical prior art implantable sensor 50 for monitoring intracranial pressure in patients. The prior art implantable sensor 50 includes a housing 52 forming a chamber 54 therein, and a cover 56 for sealing the chamber 54 of the housing 52 from the outside environment subsequent to the assembly of the prior art implantable sensor 50. The cover 56 is provided with a flexible membrane 58 integrally formed in the cover 56 as a pressure sensitive surface thereof.

The housing 52 is provided with an undercut annular lip 60 that frictionally engages an internal annular recess 62 provided by the cover 56 when the prior art implantable sensor 50 is assembled, thereby forming an overlapping joint between the housing 52 and the cover 56. The cover 56 is then secured to the housing 52 by cementing the overlapping joint together via a suitable cement.

The prior art implantable sensor 50 has a passive inductor-capacitor circuit disposed within the chamber 54 of the housing 52. The passive inductor-capacitor circuit includes a coil form 64 constructed of a non-conductive material. The coil form 64 has a suitable length of wire 66 helically wrapped around the coil form 64 thereby forming an inductor. The coil form 64 has a longitudinal bore 68 disposed therethrough configured to receive a pressure sensitive capacitor comprising a fixed capacitance plate 70, a bellows 72 having a flange 73, a bellows closure plate 74 and a tubular shaped rigid spacer 76 serving to absolutely fix the distance between the fixed capacitance plate 70 and the flange 73 when the pressure sensitive capacitor is assembled.

The bellows 72 has an open upper portion 77 and a movable closed lower portion 78. The movable closed lower portion 78 forms the pressure sensitive capacitor with the fixed capacitance plate 70 as it lies in close proximity thereto and is fixedly secured by the rigid spacer 76. The wire 66 wrapped about the coil form 64 is connected across the pressure sensitive capacitor formed by the bellows 72 and the fixed capacitance plate 70 to form the passive inductor-capacitor circuit.

The bellows 72 encloses a quantity of gas, preferably nitrogen, which is typically under pressure of one atmosphere. The gas is supplied to the bellows 72 through an aperture 80 located in the bellows closure plate 74 and is sealed therein by a pin 82 soldered in such aperture 80. The pressure sensitive capacitor has a length greater than the length of the coil form 64 so that the fixed capacitance plate 70 and the flange 74 of the bellows 72 can be forced tightly against the edges of the rigid spacer 76 by a pair of clamping plates 84 affixed to the coil form 64 by a plurality of screws 86.

When assembled, the bellows 72 is disposed within the rigid spacer 76 so that the movable closed lower portion 78 of the bellows 72 may freely reciprocate therein in response to variations in external pressure. The chamber 54 formed by the housing 52 is filled with a suitable fluid, such as a medical grade silicone fluid. As will be understood by those skilled in the art, the fluid serves to translate inward deformations of the flexible membrane 58 into compression of the bellows 72 so as to vary the capacitance of the pressure sensitive capacitor. A plurality of apertures 88 are formed in the fixed capacitance plate 70 so as to allow the fluid to freely circulate about and compress the bellows 72. Thus, body cavity pressure, such as cranial pressure, is transmitted from the flexible membrane 58 to the bellows 72 via the fluid.

It should be apparent that as pressure within the dura increases above one atmosphere, the pressure is sensed by the flexible membrane 58 of the cover 56 and is translated into a contraction of the bellows 72, and visa versa. As a result; an increase in cranial pressure will reduce the capacitance in the inductor-capacitor circuit thereby increasing the resonant frequency of the passive inductor-capacitor circuit. It should be noted that the resonant frequency of the prior art implantable sensor varies in a range from 50 MHz to 100 MHz.

When employing the prior art implantable sensor 50, problems have been encountered in that the gas enclosed by the bellows would leak through the crystalline structure of the bellows. This gas leakage decreases the pressure in the bellows 72 causing a loss of reference pressure which resulted in cranial pressure being overestimated—a process referred to in the art as baseline drift.

In addition, problems have been encountered with the prior art implantable sensor 50 in that gases (air) diffused through the housing 52 and were, thereby, absorbed in solution by the fluid. Although the increase in fluid volume due to the dissolved gas is small, the increase in fluid volume did pressurize the interior of the implantable sensor 50 formed by the housing 52 and cover 56, thereby, giving rise to additional baseline drift.

Figure 3:
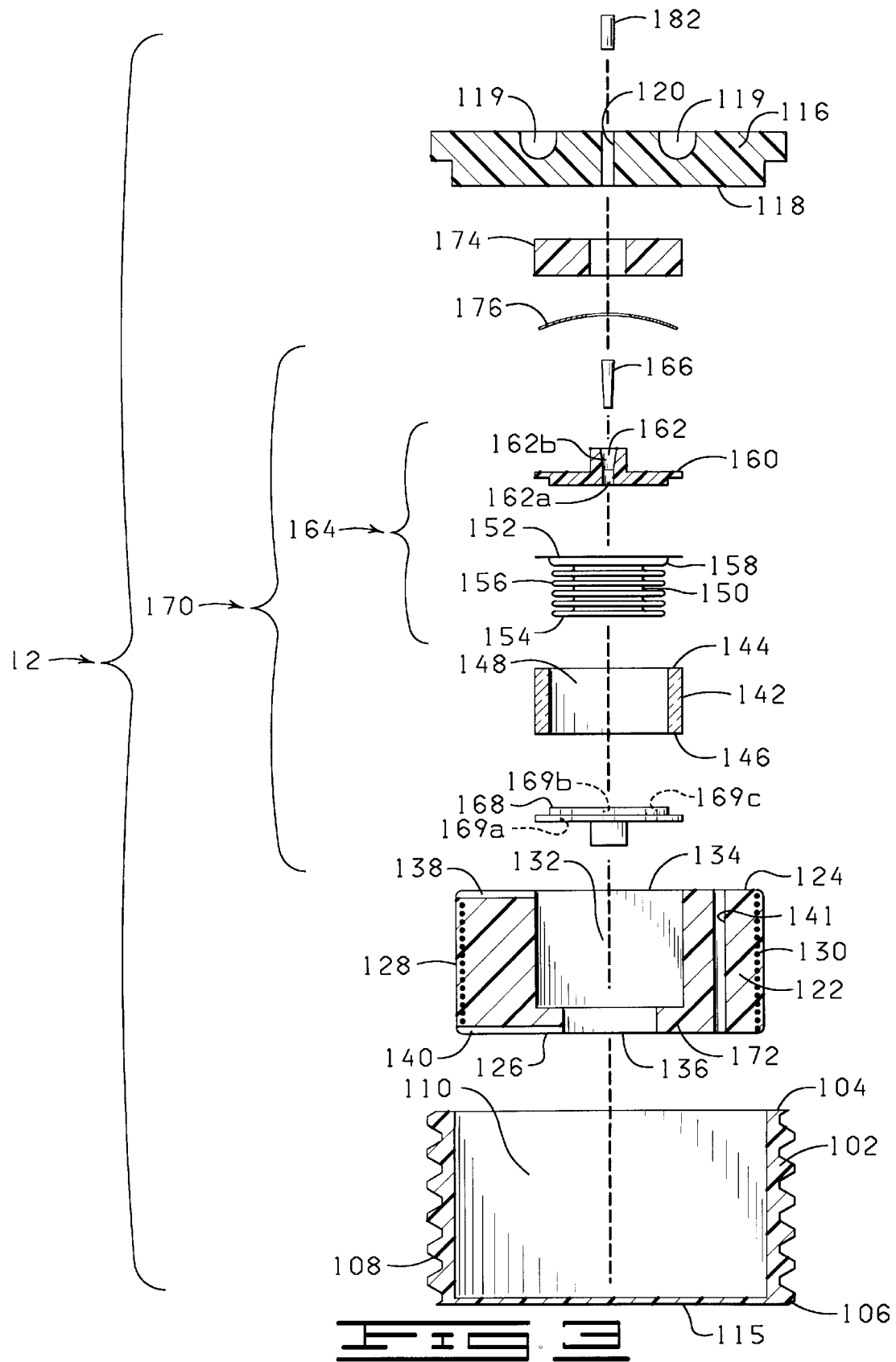
FIG. 3 is an exploded, partial cross-sectional view of an implantable sensor constructed in accordance with the present invention.
Figure 4:
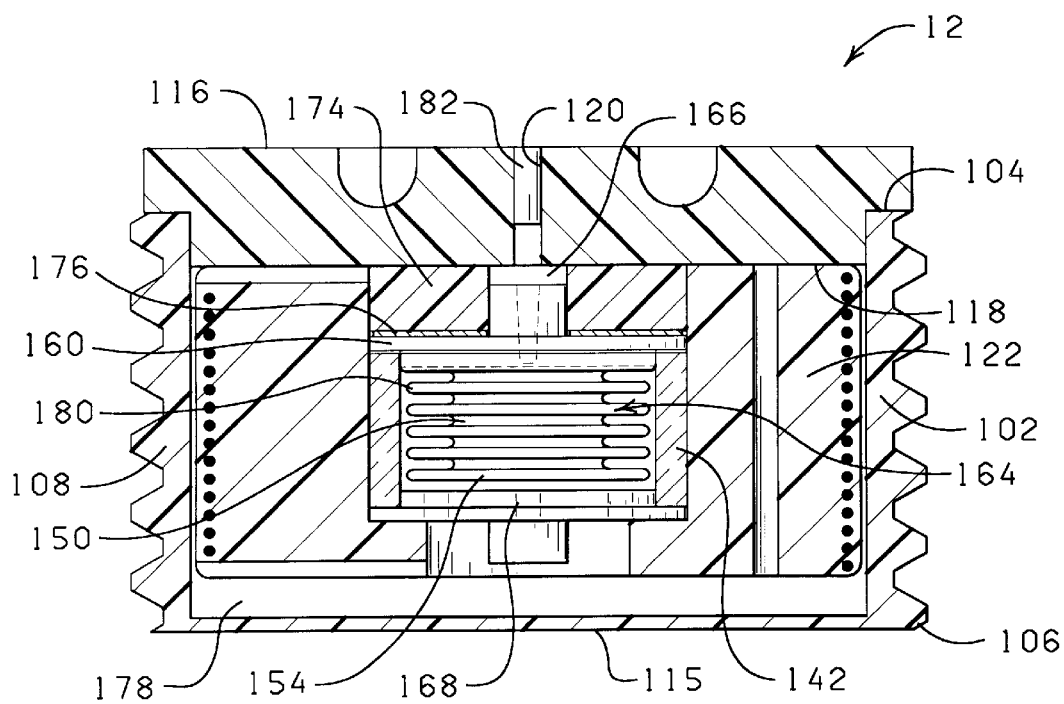
FIG. 4 is a partial, cross-sectional view of the assembled implantable sensor of FIG. 3.

Because of the problems encountered when employing the prior art implantable sensor 50, a need for an implantable sensor that has a calibration baseline which remains substantially constant throughout the life of the implantable sensor has long been recognized in the art. Referring now to FIGS. 3 and 4, the improved implantable sensor 12 constructed in accordance with the present invention is illustrated. The implantable sensor 12 overcomes the before-mentioned inherent deficiencies of the prior art implantable sensor 50 (FIG. 2); and thus the implantable sensor 12 represents an advance in the state of the art relating to implantable pressure sensors.

The implantable sensor 12 includes a housing 102 having an open upper end 104, a closed lower end 106 and a continuous sidewall 108 extending generally between the open upper and closed lower ends 104 and 106, respectively. The housing 102 typically has a length of 0.420 inches and a diameter of 0.625 inches. The closed lower end 106 and the continuous sidewall 108 of the housing 102 cooperate to provide the housing 102 with an interior surface defining a chamber 110 (FIG. 3) formed in the housing 102, the chamber 110 typically having an inside diameter of 0.480 inches. The continuous sidewall 108 of the housing 102 is threaded to cooperate with a threaded internal surface 112 (FIG. 7) provided by a mounting collar 114 (FIGS. 6 and 7) for a purpose to be described hereinafter. The closed lower end 106 of the housing 102 provides a flexible membrane 115 adapted to be positioned against the dura 30 when the implantable sensor 12 is implanted in the skull 24 of the patient 26 (FIG. 7). It should be noted that the flexible membrane 115 of the housing 102 can either be integrally formed in the housing 102 or can be a separate membrane independently securable to the housing 102. The flexible membrane 115 typically has a thickness of 0.005 inches.

The implantable sensor 12 further includes a cover 116 (FIG. 3) to seal the chamber 110 of the housing 102 from the outside environment subsequent to the assembly of the implantable sensor 12. The cover 116 has a lower surface 118, a pair of notches 119 and an aperture 120 formed therethrough for a purpose to be described hereinafter.

The implantable sensor 12 further includes a coil form 122 configured to be matingly disposed in the chamber 110 of the housing 102. The coil form 122 has an upper end 124, a lower end 126 and an outer peripheral surface 128 having a helical groove (not shown) formed therein with the helical groove typically having an intergroove space of 0.0179 inches. The coil form 122 typically has a length of 0.320 inches and a diameter of 0.480 inches.

The implantable sensor 12 further includes a suitable length of wire 130 (shown as dots) disposed in the helical groove of the coil form 122 so as to form an inductor or a coil. The wire 130 is maintained in the helical groove by filling the helical groove with a solution capable of retaining the wire 130 in the helical groove, such as a solution of polycarbonate dissolved in dichloroethane. The coil form 122 has a longitudinal bore 132 disposed therethrough with the longitudinal bore 132 having an upper end 134 and a lower end 136. The longitudinal bore 132 of the coil form 122 will be described in more detail hereinafter.

The coil form 122 has a first radial groove 138 formed in the upper end 124 of the coil form 122 and a second radial groove 140 formed in the second end 126 of the coil form 122. The first and second radial grooves 138 and 140, respectively, allow the ends of the wire 130 to pass from the helical groove into the longitudinal bore 132 formed in the coil form 122. The coil form 122 has an aperture 141 extending through the coil form 122 between the upper and lower ends 124 and 126, respectively, for allowing fluid communication between upper and lower regions of the housing 102, primarily during the vacuum filling of the implantable sensor 12 described hereinafter.

The implantable sensor 12 further includes a rigid spacer 142 having first and second opposing ends, 144 and 146, lying, respectively in first and second substantially parallel planes. The rigid spacer 142 defines a chamber 148 configured to receive a bellows 150. The bellows is constructed of an electrically conductive substance and has an open upper flange portion 152, a closed lower end plate portion 154 and an elastomeric sidewall 156 configured to fold under pressure in an accordion like manner for a purpose to be described hereinafter. The elastomeric sidewall 156 of the bellows 150 includes a step portion 158 extending outwardly a distance (typically 0.003 inches) from the elastomeric sidewall 156. The step portion 158 of the elastomeric sidewall 156 is configured to be matingly disposed in the chamber 148 of the rigid spacer 142 and serves to space the remainder of the elastomeric sidewall 156 a distance from the rigid spacer 142 so that the remainder of the elastomeric sidewall 156 can freely expand and contract within the chamber 148 without contacting the rigid spacer 142.

The implantable sensor 12 further includes a bellows closure plate 160 having a tapered aperture 162 formed therethrough. The tapered aperture 162 has a substantially cylindrical lower portion 162a and a tapered upper portion 162b. The cylindrical lower portion 162a typically has a diameter of about 0.020 inches and the tapered upper portion 162b typically has a taper of about 2.0°. The bellows closure plate 160 is attached to the open upper flange portion 152 of the bellows 150 (FIG. 4) so that the bellows closure plate 160 and the bellows 150 define a pressure sensitive chamber 164. The pressure sensitive chamber 164 provides a gas receiving cavity in the bellows 150 in communication with the tapered aperture 162 formed through the bellows closure plate 160. The bellows closure plate 160 is typically soldered to the open upper flange portion 152 of the bellows 150 via a lead-indium solder in an oxygen free, typically dry-nitrogen environment.

A compressible medium or pressure reference gas, such as dry nitrogen under pressure of one atmosphere and at standard body temperature, is supplied to the gas receiving cavity provided by the pressure sensitive chamber 164 through the tapered aperture 162 formed in the bellows closure plate 160 and is sealed therein by a tapered bellows closure pin 166 having a taper less than the taper of the upper portion 162b of the tapered aperture 162 formed in the bellows closure plate 160. The tapered bellows closure pin 166 typically has a taper of 1° and is maintained within the tapered aperture 162 via a suitable solder, such as tin-lead.

The implantable sensor further includes a fixed or first capacitance plate 168 having a plurality of apertures 169a, 169b and 169c (shown by dashed lines) formed therethrough. The rigid spacer 142 serves to secure the fixed capacitance plate 168 and the open upper flange portion 152 provided on the bellows 150 in a spaced apart, parallel relation, substantially as shown in FIG. 4. The rigid spacer 142, the bellows 150, the bellows closure plate 160, the bellows closure pin 166 and the fixed capacitance plate 168 cooperate to form a pressure sensitive capacitor 170 when assembled, as substantially shown in FIG. 4. The closed lower end plate portion 154 of the bellows 150 serves as a movable or second capacitance plate which is typically spaced about 0.003 inches apart from the fixed capacitance plate 168 when the pressure sensitive capacitor 170 is maintained at standard pressure.

The upper end 134 of the longitudinal bore 132 of the coil form 122 is configured to matingly receive the pressure sensitive capacitor 170 so that the pressure sensitive capacitor 170 can be disposed within the longitudinal bore 132 of the coil form 122. The coil form 122 further includes a shoulder portion 172 extending inwardly into the longitudinal bore 132 of the coil form 122, substantially adjacent the lower end 136 thereof. The shoulder portion 172 of the coil form 122 engages the fixed capacitance plate 168 of the pressure sensitive capacitor 170 for maintaining the pressure sensitive capacitor 170 within the longitudinal bore 132 of the coil form 122.

A passive inductor-capacitor circuit is formed by connecting one end of the wire 130 which is wrapped around the coil form 122 to the bellows closure plate 160, and an opposite end to the fixed capacitance plate 168 of the pressure sensitive capacitor 170.

The implantable sensor 12 further includes a spring retainer 174 configured to be matingly disposed in the longitudinal bore 132 of the coil form 122 for engaging a spring washer 176. The spring retainer 174 and the spring washer 176 form a bias means for holding the bellows 150, the capacitance plate 168 and the rigid spacer 142 in slight compression when the implantable sensor 12 is assembled (FIG. 4). The spring retainer 174 is maintained in the longitudinal bore 132 of the coil form 122 via a solution capable of retaining the spring retainer 174 in the longitudinal bore 132, such as a solution of polycarbonate and dichloroethane. It should be noted that the coil form 122 has a length greater than the length of the pressure sensitive capacitor 170 so that the pressure sensitive capacitor 170 is housed entirely within the coil form 122 and held in slight compression between the spring retainer 174 and the shoulder portion 172 of the coil form 122.

Once assembled (FIG. 4), the implantable sensor 12 has a first fluid receiving cavity 178 defined by the lower end 126 of the coil form 122 and the flexible membrane 115 of the housing 102, and a second fluid receiving cavity 180 surrounding the bellows 150. The fixed capacitance plate 168 is interposed between the first and second fluid receiving cavities 178 and 180, respectively, which fluidly communicate via the apertures 169a, 169b, and 169c formed through the fixed capacitance plate 168.

The first and second fluid receiving cavities 178 and 180, respectively, are completely filled with a quantity of a suitable fluid, such as a medical grade silicone fluid, through the aperture 120 formed in the cover 116. The first and second fluid receiving cavities 178 and 180, respectively, are then sealed by disposing a plug 182 into the aperture 120. The plug 182 is maintained in the aperture 120 with a solution capable of retaining the plug 182 in the aperture 120, such as a solution of polycarbonate and dichloroethane.

Because the housing 102 and the cover 116 are both constructed of rigid materials, the fluid and the flexible membrane 115 serve as a pressure responsive means for communicating the actual pressure within the cavity in the patient 26 to the pressure sensitive chamber 164. In other words, the fluid transmits or communicates deformations of the flexible membrane 115 into compression of the bellows 150. As actual body cavity pressure is transmitted to the fluid via the flexible membrane 115, the fluid transmits or communicates the actual body cavity pressure to the bellows 150 such that the pressure reference gas and the elastomeric sidewall 156 of the bellows 150 oppose the actual body cavity pressure and vary the distance between the fixed capacitance plate 168 and the closed lower end plate portion 154 of the bellows 150 accordingly. In other words, as actual body cavity pressure increases, the elastomeric sidewall 156 of the bellows 150 is compressed and thus, the gap between the fixed capacitance plate 168 and the closed lower end plate portion 154 is increased thereby decreasing the capacitance of the pressure sensitive capacitor 170 and increasing the resonant frequency of the passive inductor-capacitor circuit. Likewise, as actual body cavity pressure decreases, the bellows 150 is expanded and the distance between the fixed capacitance plate 168 and the closed lower end plate portion 154 of the bellows 150 is decreased thereby increasing the capacitance of the pressure sensitive capacitor 170 and decreasing the resonant frequency of the passive inductor-capacitor circuit. It should be noted that the pressure reference gas contained within the pressure sensitive chamber 164 and the elastomeric sidewall 156 of the bellows 150 form a spring constant of the pressure sensitive chamber 164. The pressure reference gas accounts for about 10% of the spring constant of the pressure sensitive chamber 164 and the elastomeric sidewall 156 accounts for the other 90% of such spring constant.

The housing 102, cover 116, coil form 122 and spring retainer 174 of the implantable sensor 12 are typically machined from a rigid, non-porous, non-conductive material, such as biocompatible plastic. The biocompatible plastic can be a polysulfone or a polycarbonate obtainable from Westlake Plastics, Inc.

Figure 5:
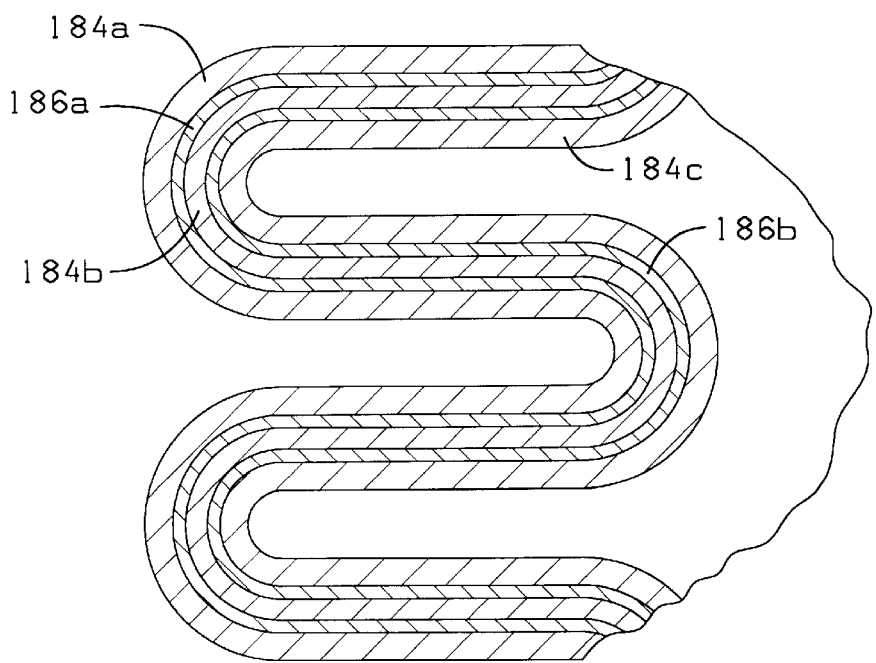
FIG. 5 is a fragmental, cross-sectional view of a bellows constructed in accordance with the present invention.

Shown in FIG. 5 is a fragmentary, cross-sectional view of the elastomeric sidewall 156 of the bellows 150. The bellows 150 is typically constructed by an electrodeposition process which is well known in the art. The bellows 150 is electroformed as alternating layers of a first metal 184 and a second metal 186. The layers of the first metal are designated in FIG. 5 as 184a, 184b and 184c, and the layers of the second metal are designated in FIG. 5 as 186a and 186b. Typically, the first metal is nickel and the second metal is copper. As will be understood by those skilled in the art, the layers of the second metal 186 are preferably flashed at the one-third points in the elastomeric sidewall 156 of the bellows 150 to cause the crystalline growth pattern of the first metal 184 to be changed twice during the construction of the bellows 150 thereby resulting in much smaller crystals and thereby much lower porosity. It should be understood that any number of alternating layers of the first and second metals 184 and 186, respectively, can be utilized to form the bellows 150 of the present invention so long as at least 2 layers of the second metal 186 are utilized. The bellows 150 of the implantable sensor 12 are obtainable from Servometer corporation, 501 Little Falls Road, Cedar Grove, N.J. 07009.

The fixed capacitance plate 168, bellows closure plate 160 and bellows closure pin 166 are typically constructed of brass, and the spring washer 176 is typically constructed of beryllium copper.

The rigid spacer 142 is desirably tubular in shape and can be constructed of a quartz glass or any other rigid non-conductive material which maintains a high degree of dimensional stability. The rigid spacer 142 can be a pyrex spacer obtainable from Precision Electronic Glass of New Jersey. It should be noted that the inner edge at both ends of the rigid spacer 142 are desirably chamfered to accommodate the corner radius of the pressure sensitive chamber 164 and fixed capacitance plate 168 of the pressure sensitive capacitor 170.

When the implantable sensor 12 is implanted within a cavity for extended periods, a small amount of moisture may diffuse through the housing 102 of the implantable sensor 12. It is important to note that the bellows 150, bellows closure plate 160, bellows closure pin 166, fixed capacitance plate 168 and spring washer 176 are all preferably gold plated so as to prevent such components from tarnishing due to such moisture.

The assembly of the implantable sensor 12 will now be described. First, the bellows closure plate 160 is soldered to the open upper flange portion 152 of the bellows 150 via a solder capable of connecting the bellows closure plate 160 to the open upper flange portion 152 of the bellows 150, such as a lead-indium solder. The pressure sensitive chamber 164 is then filled with the pressure reference gas, typically dry nitrogen, by placing the pressure sensitive chamber 164 in a sealed hyperbaric chamber held at body temperature in an incubator (now shown). A complete vacuum is pulled on the hyperbaric chamber while containing a plurality of bellows 150 having the bellows closure plate 160 attached thereto and the aperture 162 of the bellows closure plate 160 open. The hyperbaric chamber pressure is raised to about two atmospheres with dry nitrogen and is then completely evacuated. Then, the hyperbaric chamber pressure is again raised to above standard atmospheric pressure and is slowly reduced to standard atmospheric pressure. At this pressure, the pressure sensitive chamber 164 is sealed by lightly tapping the bellows closure pin 166 into the tapered aperture 162 formed in the bellows closure plate 160. Once sealed, the pressure sensitive chamber 164 is removed from the incubator and the bellows closure pin 166 is stabilized in the tapered aperture 162 via a suitable solder, such as a tin-lead solder. The excess length of the bellows closure pin 166 is then trimmed off flush with the bellows closure plate 160.

The pressure sensitive capacitor 170 is assembled by disposing the fixed capacitance plate 168 and the bellows 150 in the chamber 148 of the rigid spacer 142, substantially as shown in FIG. 4. Then, the pressure sensitive capacitor 170 is connected to a standard inductance coil so that the pressure sensitive capacitor 170 can be calibrated by changing the length of the rigid spacer 142 and/or the thickness of the fixed capacitance plate 168. It should be noted that the dimensionally stable rigid spacer 142 prevents the capacitance of the pressure sensitive capacitor 170 from being disturbed by assembling the rest of the implantable sensor 12.

It will be appreciated by those skilled in the art that because the gap between the fixed capacitance plate 168 and the closed lower end plate portion 154 of the bellows 150 is filled with air rather than a silicone fluid, for example, the resonant frequency must be adjusted to 1.62 times the desired resonant frequency. Typically, the resonant frequency of the passive inductor-capacitor circuit is adjusted to about 60 MHz in air so that the "in fluid" resonant frequency of such circuit is about 40.0 MHz.

The pressure sensitive capacitor 170, spring washer 176 and spring retainer 174 are then positioned in the longitudinal bore 132 of the coil form 122 substantially as shown in FIG. 4. A fixture (not shown) is utilized to hold the pressure sensitive capacitor 170, spring washer 176 and spring retainer 174 in a slight compression while the spring retainer 174 is bonded to the coil form 122 via a solution capable of connecting the spring retainer 174 to the coil form 122, such as a solution of polycarbonate and dichloroethane. After the spring retainer 174 is bonded to the coil form 122, one end of the wire 130, which is wrapped around the coil form 122, is connected to the bellows closure plate 160 while an opposite end of the wire 130 is connected to the fixed capacitance plate 168 by any suitable method, such as by soldering one of the ends of the wire 130 to a first brass split ring (not shown) and an opposite end of the wire 130 to a second brass split ring (not shown). The first split ring is attached to a portion of the bellows closure plate 160 and the second split ring is attached to a portion of the fixed capacitance plate 168.

The upper end 124 of the coil form 122 is then bonded to the lower surface 118 of the cover 116 via a solution capable of connecting the coil form 122 to the cover 116, such as a solution of polycarbonate and dichloroethane. The coil form 122 is inserted into the chamber 110 of the housing 102 until the cover 116 engages the housing 102. In this position, the passive inductor-capacitor circuit and cover 116 are maintained within the chamber 110 of the housing 102 by bonding the cover 116 to the housing 102 via a solution capable of bonding the cover 116 to the housing 102, such as a solution of polycarbonate and dichloroethane.

The implantable sensor 12 is then held in air for several days to permit the dichloroethane to diffuse out of the polycarbonate. It should be noted that the housing 102, cover 116, coil form 122 and spring retainer 174 are all bonded together to form a rigid, nearly unitary structure.

Figure 8:
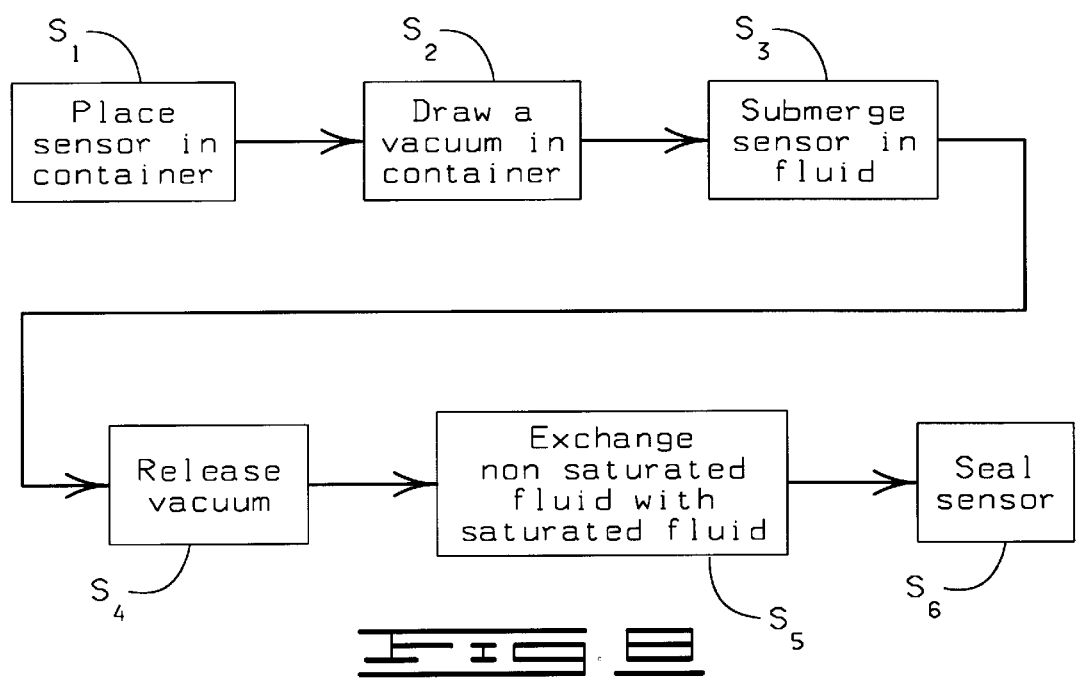
FIG. 8 is a diagrammatic view illustrating the manner in which the implantable sensor is filled with a fluid.

As shown diagrammatically in FIG. 8, at a step S1, the implantable sensor 12 is filled with fluid by first disposing the implantable sensor 12 and the fluid within a sealed container. Then, at a step S2, a vacuum is drawn in the sealed container and held for a period to remove as much air and water vapor as possible before the implantable sensor 12 is submerged in the fluid. It should be understood that the period that the vacuum is held in the sealed container can vary widely so long as the vacuum removes as much air and water vapor as possible. Generally, however, the vacuum is held in the sealed container for about 1 hour.

At a step S3, the implantable sensor 12 is submerged in the fluid and the vacuum is maintained until bubbles cease to be emitted from the aperture 120 of the cover 116. At a step S4, the vacuum in the container is slowly released back to atmospheric pressure to allow the fluid to migrate into the implantable sensor 12 through the aperture 120 formed in the cover 116 of the implantable sensor 12. Typically, the vacuum is released back to atmospheric pressure over a period of 1 hour.

The vacuum filling process described above removes virtually all of the dissolved and entrained air from the fluid. Sealing the implantable sensor 12 in this condition results in a severe baseline drift due to air diffusing through the housing 102 and being dissolved into the fluid. Thus, at a step 5, the fluid within the implantable sensor 12 is exchanged with a fluid saturated with gas at a temperature substantially equal to standard body temperature (37° C.). The fluid can be exchanged by leaving the implantable sensor 12 submerged within the fluid for several weeks while holding the container at standard body temperature. Another method for exchanging the fluid within the implantable sensor 12 is to deliberately inject saturated fluid into the implantable sensor via a hypodermic syringe, for example, while holding the implantable sensor at standard body temperature.

After the fluid within the implantable sensor 12 has been exchanged, the implantable sensor is sealed by disposing the pin 182 into the aperture 120 formed in the cover 116 of the implantable sensor 12, as previously discussed.

One method in which the implantable sensor 12 may be disposed within the skull 24 of the patient 26 is illustrated in detail in FIGS. 6 and 7. The mounting collar 114 is positioned over a burr hole 202 formed in the skull 24 of the patient 26 by known techniques. For instance, an air driven trephine or brace trephine can be used to make the burr hole, the cavity of the skull being trimmed with a curette to expose a circular area of dura. Bone wax is used to reduce bleeding from the walls of the burr hole and a bipolar coagulator could be used to stop any bleeding which may exist on the surface of the exposed dura 30. Once the burr hole 202 is formed, the mounting collar 114 is attached to the skull 24 via a pair of apertures (not shown) which accommodate a pair of skull screws or sutures 203 to permit affixment of the mounting collar 114 to the skull 24. The mounting collar 114 provides a neck 204 into which the housing 102 of the implantable sensor 12 may be threaded. The notches 119 provided in the cover 116 of the implantable sensor 12 can be engaged by a suitable tool to facilitate threading of the implantable sensor 12 into the neck 204 of the mounting collar 114. The implantable sensor 12 is inserted into the mounting collar 114 sufficiently to have the flexible membrane 115 of the implantable sensor 12 in contact with the dura 30. This is typically accomplished by measuring the distance from the top of the collar 114 to the surface of the dura 30 and then increasing the insertion distance of the implantable sensor 12 by 0.5 to 1.0 millimeters. It should be apparent to one skilled in the art that other structures and methods may be employed to position the implantable sensor 12 of the present invention within the skull 24 of the patient 26.

Laboratory tests were conducted utilizing implantable sensors, such as the implantable sensor 12. Testing was performed in a simulated implantation environment consisting of a closed hyperbaric chamber located within an incubator which maintained the sensors at body temperature at all times. A nitrogen pressure source and a vacuum pump were vented to the hyperbaric chamber through the incubator wall. The sensors were further maintained at atmospheric pressure when data was not being collected and standard sea level pressure when data was being collected.

Three lots of sensors (designated Lot I, Lot II and Lot III) were fabricated and drift tested in the simulated implantation environment. Lot I sensors were substantially similar in construction as the implantable sensor 12, except that the housing 102 was not sealed. Lot I sensors were retained in a silicone oil bath for isolating any drift due to bellows porosity from that drift resulting from case pressurization due to air diffusing through the housing. It was found that in 323 days of testing, Lot I sensors did not drift out of a pressure control uncertainty band of 0.015 mm Hg/day thereby confirming that the bellows 150 of the present invention substantially eliminated the baseline drift due to bellows porosity associated with prior art sensors.

Lot II sensors were substantially similar in construction as the implantable sensor 12 except that the housings of such sensors were sealed without exchanging the unsaturated fluid contained within such sensors with saturated fluid. The Lot II sensors exhibited a very rapid initial baseline drift rate up to a final pressure offset of approximately 40 mm Hg.

Lot III sensors were substantially similar in construction as the implantable sensor 12 except that only a rudimentary attempt was made to exchange the fluid within the sensors with fluid saturated with gas at standard body temperature and standard pressure. The lot III sensors exhibited an initial baseline drift smaller than the baseline drift exhibited by the lot II sensors. Thus, it was found that the baseline drift due to gases diffusing through the housing was quite manageable by exchanging the fluid within the sensor with fluid saturated with gases at standard body temperature and standard pressure.

In summary, the results of these tests conclusively show that sensors constructed in accordance with the present invention provide dramatically less baseline drift and therefore superior performance than the prior art sensors, such as the sensor disclosed in U.S. Pat. No. 4,265,252, issued to Chubbuck et al. on May 5, 1981. In fact, the implantable sensor 12 has a calibration baseline that remains substantially constant throughout the life of the implantable sensor 12. The calibration baseline of the implantable sensor 12 does not drift more than 0.015 mm Hg/day.

Figure 9:
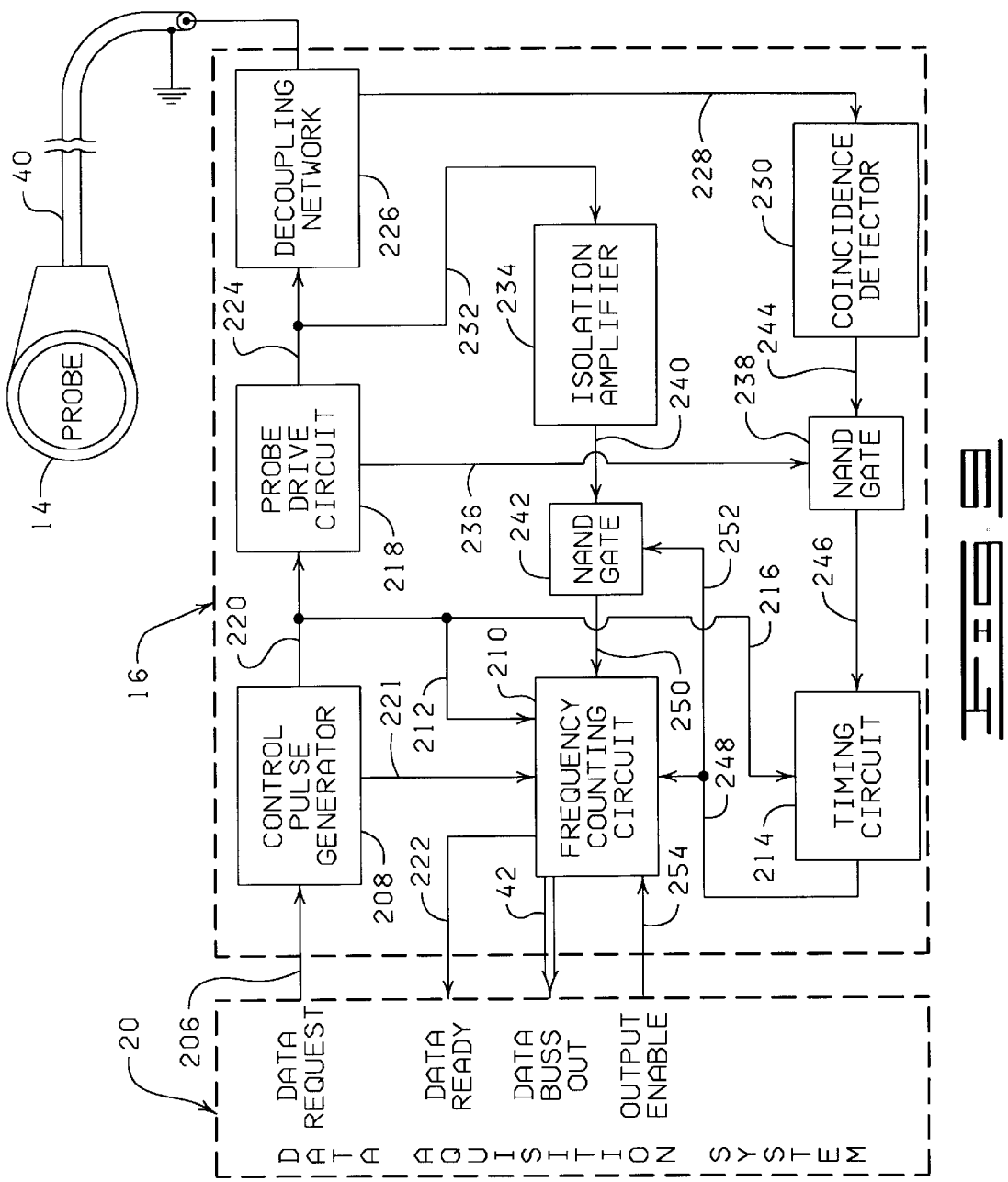
FIG. 9 is a diagrammatic, schematic view illustrating a probe, a data acquisition system and an interrogation circuit of the telemetric intracranial pressure monitoring system.

The interrogation circuit 16 will now be discussed in more detail. As illustrated in FIG. 9, data indicative of the resonant frequency of the implantable sensor 12 is requested by the data acquisition system 20 by providing a signal over a signal path 206 (FIG. 9) to be received by the input of a control pulse generator 208 (FIG. 9) which is typically an integrated circuit such as a 74LS221 monostable multivibrator. In response to receiving the signal from the data acquisition system 20, the control pulse generator 208 provides an adequate pulse to clear a frequency counting circuit 210 (FIGS. 9 and 12) via signal path 212, to clear a timing circuit 214 (FIGS. 9 and 13) via signal path 216, and to trigger a probe drive circuit 218 (FIGS. 9 and 10) via signal path 220. Further, the control pulse generator 208 outputs a signal over signal path 221 to be received by the frequency counting circuit 210. In response thereto, the frequency counting circuit 210 toggles the "data ready flag" output to the data acquisition system 20 via signal path 222 so that the data acquisition system will know not to request data until the "data ready flag" has been reset after the frequency counting circuit 210 has finished counting.

Figure 11:
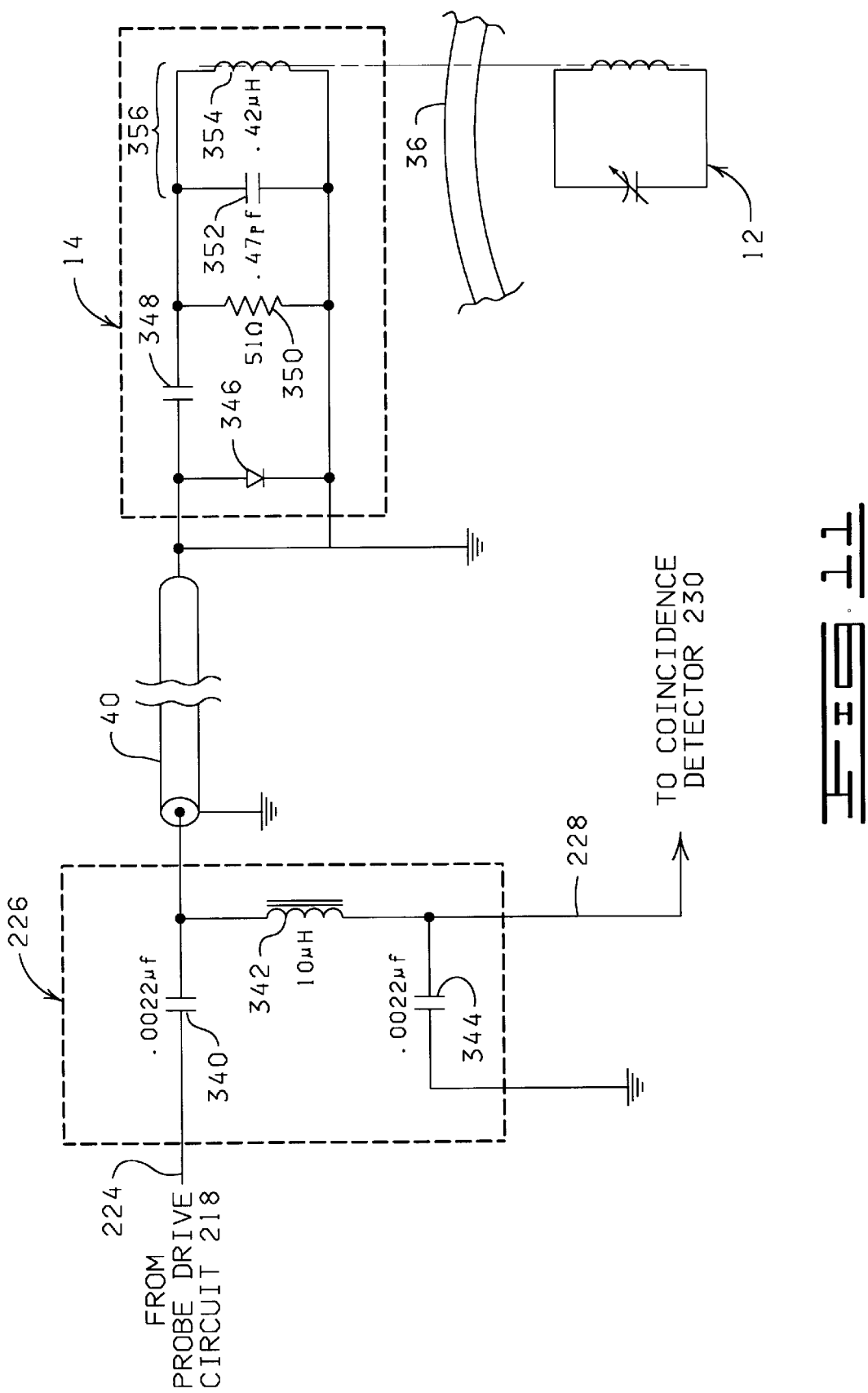
FIG. 11 is a diagrammatic, schematic view illustrating a decoupling network of the interrogation circuit and the probe of the present invention.

The probe 14 is connected by signal path 224 to the probe drive circuit 218 through a decoupling network 226 (FIGS. 9 and 11). The probe 14 is also connected via a signal path 228 to a coincidence detector 230 (FIGS. 9 and 13) through the decoupling network 226. Upon receiving the pulse from the control pulse generator 208 via signal path 220, the probe drive circuit 218 outputs the RF input signal via signal path 224 to the decoupling network 226 which passes the RF input signal to the probe 14 via signal path 40 and then passes the returning DC probe output signals detected by the probe 14 to the coincidence detector 230 via signal path 228. The probe drive circuit 218 is also connected via signal path 232 to an isolation amplifier 234 (FIGS. 9 and 12) and via signal path 236 to a NAND gate 238 (FIGS. 9 and 13) for a purpose to be described hereinafter. It should be noted that the NAND gate 238 is typically a Schmitt trigger NAND gate, such as an SN74S132.

Figure 12:
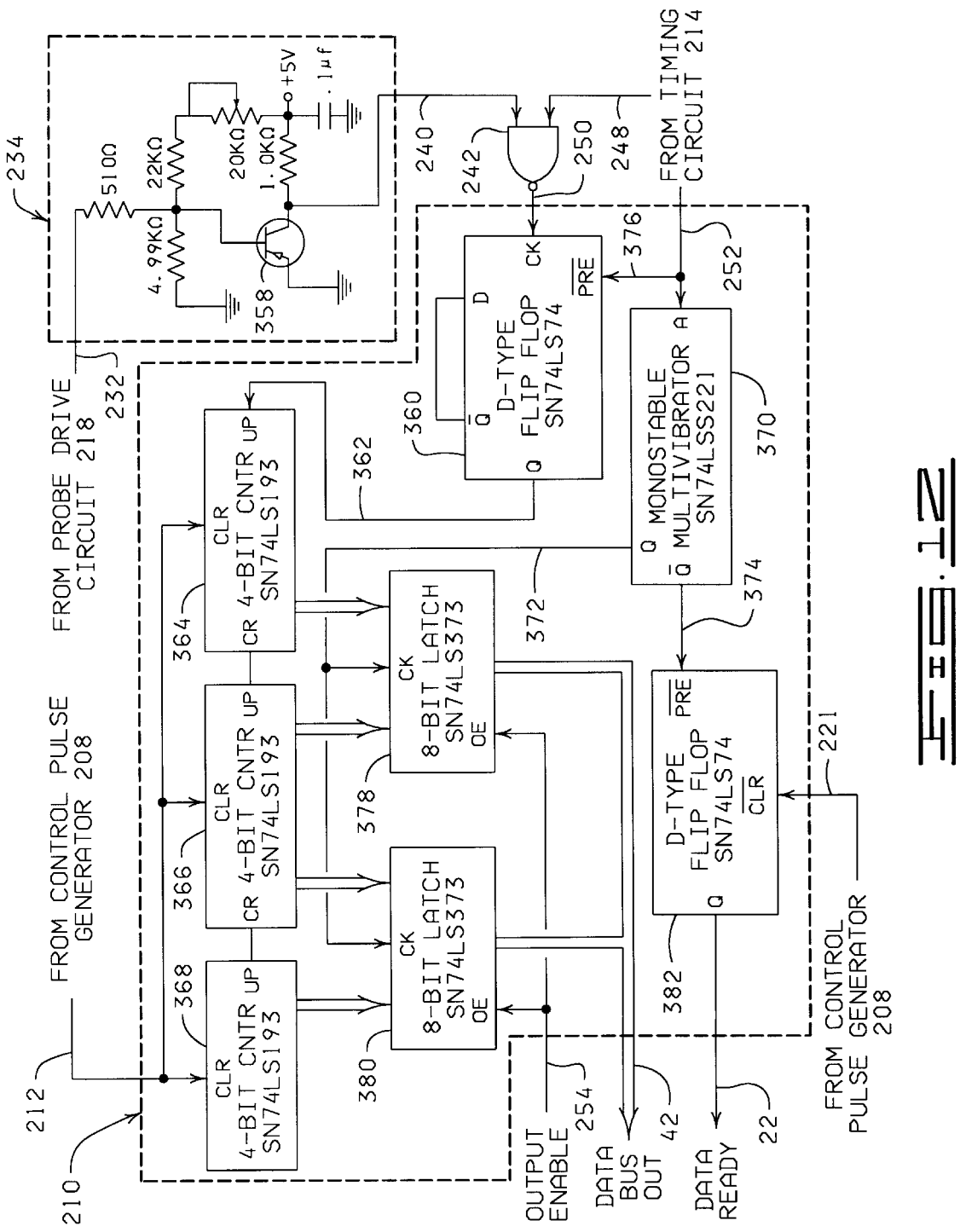
FIG. 12 is a diagrammatic, schematic view illustrating a frequency counting circuit and an isolation amplifier of the interrogation circuit of the present invention.

The isolation amplifier 234 receives the RF input signal from the probe drive circuit 218 and in response thereto, converts the RF input signal into a standard digital TTL signal having the same frequency as the RF input signal. The isolation amplifier 234 outputs the standard digital TTL signal over a signal path 240 to be received by one input of a NAND gate 242 (FIGS. 9 and 12).

In normal operation, the RF input signal output by the probe drive circuit 218 is swept substantially linearly from 25 MHz to 50 MHz in 4 ms and then rests at 50 MHz for 1 ms to form a 5 ms "forward sweep period" of the RF input signal. The frequency of the RF input signal is then swept back from 50 MHz to 25 MHz in about 4 ms to form a "flyback period" of the RF input signal. Desirably, the probe 14 has a very low quality factor "Q" so that the output power level is maintained at a constant level over the 25 to 50 MHz sweep range to within ±0.25 db. In the absence of inductive coupling, the RF voltage of the probe 14 remains substantially constant throughout the sweep range. The resulting DC probe output voltage likewise remains constant.

In operation, the probe 14 is placed over a location on the scalp 36 of the patient 26 near where the implantable sensor 12 is implanted. The resonant frequency of the implantable sensor 12 and thus the cranial pressure is then determined by subjecting the implantable sensor 12 to a frequency swept magnetic field generated by the probe 14 which encompasses the resonant frequency of the implantable sensor 12.

When the frequency of the magnetic field is coincident with the resonant frequency of the implantable sensor 12, the implantable sensor 12 absorbs energy from the magnetic field thereby causing a maximum energy transfer from the probe 14 to the implantable sensor 12 only at the resonant frequency of the implantable sensor 12. When this maximum energy transfer occurs, an accompanying reduction (dip) in the voltage of the RF input signal appears across the probe 14 and likewise, an accompanying dip appears in the voltage of the DC probe output signal output by the probe 14 to the coincidence detector 230. This reduction can be envisioned as an energy transfer which loads down the source of the voltage, i.e. the probe drive circuit 218.

The magnitude of the RF voltage dip or reduction depends primarily on the amount of inductive coupling between the inductors of the probe 14 and the implantable sensor 12 when the inductors are positioned in the closest possible proximity. The maximum energy transfer occurs only at the resonant frequency of the implantable sensor 12;

consequently, as the RF input signal is swept across the operating frequency, the DC output signal generated by the probe 14 will exhibit only one voltage dip as the frequency of the RF input signal passes through the resonant frequency of the implantable sensor 12.

The bandwidth of this voltage dip is determined solely by the "Q" of the inductor-capacitor circuit of the implantable sensor 12. By correlating the frequency of the RF input signal with the occurrence of the lowest point of the voltage dip, the resonant frequency of the implantable sensor 12 is determined, the cranial pressure being related thereto.

As mentioned above, the coincidence detector 230 receives the DC output signal generated by the probe 14 and detects the occurrence of the voltage dip. When the voltage dip occurs, the coincidence detector 230 generates and outputs a signal over signal path 244 to be received by the NAND gate 238.

During the "forward sweep period" of the RF input signal, the probe drive circuit 218 holds one input of the NAND gate 238 high via signal path 236 so that when the voltage dip occurs the signal output by the coincidence detector 230 via signal path 244 is inverted by the NAND gate 238 and passed therethrough to the timing circuit 214 via signal path 246.

In response to receiving the signal generated by the coincidence detector 230, the timing circuit 214 outputs a high-level signal for a predetermined time (referred to hereinafter as the ("ecounting period") over signal path 248 to be received by the NAND gate 242. In response thereto, the NAND gate 242 is held open for the counting period so that the standard digital TTL signal output by the isolation amplifier 234 passes through the NAND gate 242 and is received by the frequency counting circuit 210 via signal path 250.

The frequency counting circuit 210 counts the cycles of the standard digital TTL signal for the counting period thereby creating a digital output signal proportional to the pressure sensed by the implantable sensor 12. After the frequency counting circuit 210 has finished counting the standard digital TTL signal, the timing circuit 214 outputs a pulse to the frequency counting circuit 210 via signal path 252. Upon receiving the pulse from the timing circuit 214, the frequency counting circuit 210 latches the digital output signal and outputs a signal over signal path 222 to reset the data ready flag and thereby tell the data acquisition system 20 that the digital output signal is ready to be transmitted via the signal path 42. In response thereto, the data acquisition system 20 outputs an output enable signal over signal path 254 so that the frequency counting circuit 210 will transmit the digital output signal to the data acquisition system 20 via the signal path 42.

Figure 10:
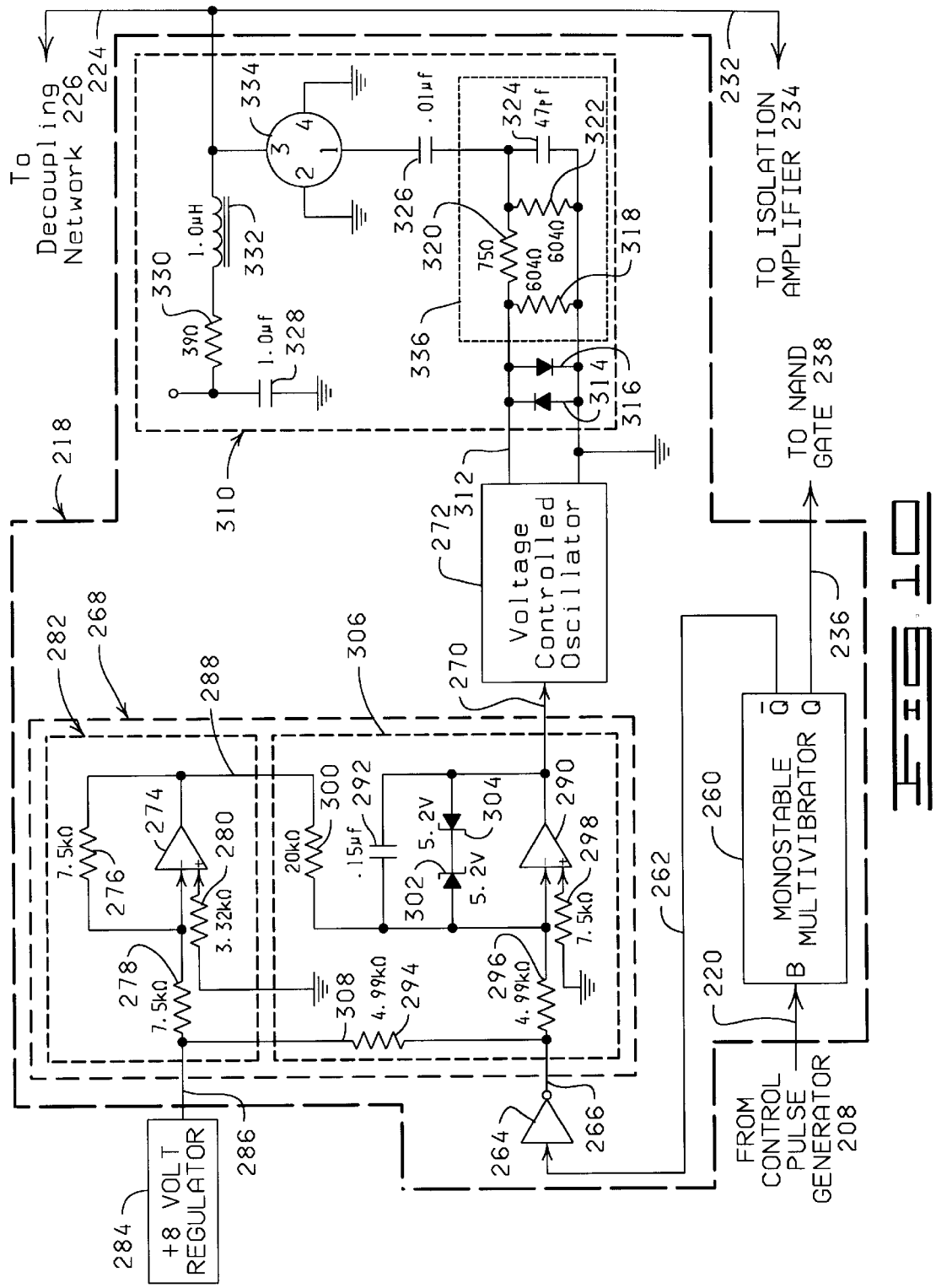
FIG. 10 is a diagrammatic, schematic view illustrating a probe drive circuit of the interrogation circuit of the present invention.

The probe drive circuit 218 is shown in FIG. 10. A monostable multivibrator 260 (FIG. 10) having a predetermined time constant, typically of 5 ms, receives the pulse output by the control pulse generator 208 via signal path 220. In response thereto, the monostable multivibrator 260 outputs a high-level pulse over signal path 236 to be received by the NAND gate 238 (FIGS. 9 and 13) and a low-level pulse over a signal path 262 to be received by an open-collector high voltage inverter 264 (FIG. 10). The open-collector high voltage inverter 264 outputs a high-level pulse over a signal path 266 to be received by a sweep voltage generator 268 (which is shown in FIG. 10 by the dotted lines). Upon receiving the high-level pulse, the sweep voltage generator 268 outputs a control signal sweeping from +5 V to −5 V in approximately 4 ms or −2.50 V/ms over a signal path 270 to be received by a voltage controlled oscillator 272 (FIG. 10).

The sweep voltage generator 268 has an amplifier 274, a resistor 276, a resistor 278 and a resistor 280 forming an inverting amplifier 282 typically having a gain of −1.0 V/V. The inverting amplifier 282 is electrically connected to a voltage regulator 284 (FIG. 10) via a signal path 286. The voltage regulator 284 outputs a constant voltage, typically of about +8.0 volts over signal path 286 to be received by the inverting amplifier 282. As a result, the inverting amplifier 282 inverts the constant voltage received from the voltage regulator 284 and outputs a regulated −8.0 volt signal over a signal path 288.

The sweep voltage generator 268 is further provided with an amplifier 290, a capacitor 292, a resistor 294, a resistor 296, a resistor 298, a resistor 300, a zener diode 302 and a zener diode 304 forming an integrator 306 (FIG. 10). The integrator 306 receives the inverted signal output by the inverting amplifier 282 via signal path 288, receives the signal output by the open-collector high voltage inverter 264 via signal path 266 and receives the signal output by the voltage regulator via signal path 308.

When the output of the open-collector high voltage inverter 264 is at low-level, the resistor 300 is the only input function to the integrator 306. Thus, the output of the amplifier 290 increases (positively) until the zener diode 302 terminates the output at +5.0 volts. However, during the forward sweep period of the probe drive circuit 218 when the output of the open-collector high voltage inverter 264 is at high-level, the exact output voltage of the open-collector high voltage inverter 264 is defined by the circuitry connected thereto. Thus, the output of the voltage regulator 284 becomes an input to the amplifier 290 through resistors 294 and 296. Since the conductance of resistors 294 and 296 is twice that of resistor 300, the net input to the operational amplifier 290 causes the output of the integrator 306 to proceed linearly from +5.0 volts to −5.0 volts during the first 4.0 millisecond of the 5.0 millisecond forward sweep period. At this time, the frequency output by the voltage controlled oscillator 272 reaches 50.0 MHZ.

The amplifier output is held at −5.0 volts for approximately 1.0 millisecond by the zener diode 304. At the termination of the 5.0 millisecond period of the low-level signal output by the monostable multivibrator 260 via signal path 262, the output of the open-collector high voltage inverter 264 goes to low-level allowing the output of the integrator 306 to return to +5.0 volts where it remains until the onset of the next data request.

The voltage controlled oscillator 272 can be a Vectron 371Y1281, obtainable from Vectron, Inc. of Norwalk, Conn. The voltage controlled oscillator 272 has an inverse transfer function in that its output frequency increases as the input control voltage decreases (becomes more negative).

The output of the voltage controlled oscillator 272 is typically regarded as only a frequency. That is, for a predetermined input voltage, the voltage controlled oscillator 272 outputs a predetermined output frequency. However, the voltage output of the voltage controlled oscillator 272 can vary depending upon the output frequency and the loading of the voltage controlled oscillator 272. Typically, the output voltage level of the voltage controller oscillator 272 will vary by a factor of three over the frequency range of 25 to 50 MHz. Thus, the output of the voltage controlled oscillator is connected to a leveling amplifier 310 (FIG. 10) via signal path 312.

The levelling amplifier 310 is formed by a diode 314, a diode 316, a resistor 318, a resistor 320, a resistor 322, a capacitor 324, a capacitor 326, a capacitor 328, a resistor 330, an inductor 332 and an amplifier 334. The levelling amplifier 310 receives the signal output by the voltage controlled oscillator 272 and generates the RF input signal output via signal path 224 to be received by the decoupling network 226 (FIGS. 9 and 11).

The diodes 314 and 316 clip both the positive and negative peaks of the output of the voltage controlled oscillator 272 at approximately 0.3 volts. Because the output of the voltage controlled oscillator 272 is clipped symmetrically and because the voltage controlled oscillator 272 has a 50—50 duty cycle, the lowest harmonic frequency generated by the clipping process is -the third harmonic. Even when operating near the low end of the frequency scale (25 Hz), the generated harmonics all fall above the frequency range of interest.

The resistors 318, 320 and 322 and capacitor 324 form a low pass filter 336. The low pass filter 336 rounds the clipped output of the voltage controlled oscillator 272 into a substantially sinusoidal shape.

The amplifier 334 is typically a MAV11 monolithic amplifier obtainable from Mini-Circuits, of Brooklyn, N.Y. The amplifier 334 typically has a gain of about 12.7 dbm when the amplifier 334 is loaded by the probe 14 through the decoupling network 226 (FIGS. 9 and 11) and the signal path 40.

One embodiment of the decoupling network 226 is shown in FIG. 11. The decoupling network 226 essentially consists of a low RF impedance capacitor 340 which passes the RF input signal from the probe drive circuit 218 to the probe 14 via signal path 40 and which simultaneously blocks the DC output signal generated by the probe 14. The decoupling network 226 further includes a rf choke or inductor 342 which shunts the DC output signal generated by the probe 14 to the coincidence detector 230 (FIGS. 9 and 13) via signal path 228 and which simultaneously presents a very high impedance to the RF input signal. The decoupling network 226 further includes a low RF impedance capacitor 344 positioned between the RF choke 342 and the coincidence detector 230 which serves to filter any stray RF input signals out of the DC output signal so that the stray RF input signals are not passed to the coincidence detector 230.

One embodiment of the probe 14 is also shown in FIG. 11. The probe 14 is provided with a diode 346, a capacitor 348, a resistor 350, a capacitor 352 and an inductor 354. The resistor 350 terminates the signal path 40 in its characteristic impedance so as to minimize the standing wave ratio of the probe 14 and to thereby minimize reflections which can obscure the loading effects of the RF input signal. Although separate coaxial cables could be used to separately convey the RF input signal and the DC output signal, the presence of two separate cables attached to the probe 14 results in inflexibility of the combination and is less easy to use for routine monitoring.

The capacitor 352 and the inductor 354 of the probe 14 form a parallel resonant circuit 356 typically tuned to about 35.36 MHz (the logarithmic mean of 25 and 50 MHz). The parallel resonant circuit 356 has a very low "Q" due to the resistor 350 which results in the voltage across the parallel resonant circuit 356 remaining substantially constant while the frequency is being swept from 25 MHz to 50 MHz. The inductor 354 is typically a three turn coil printed on a printed circuit board and typically has an inductance of about 0.42 $\mu$h. The capacitor 352 typically has a capacitance of 47 pf.

The diode 346 is placed across the signal path 40 and in parallel with the resonant circuit 356 for rectifying the RF input signal received by the probe 14 and thereby generating the DC output signal. It should be noted that the voltage of the -DC output signal is proportional to the peak-to-peak voltage amplitude of the RF input signal. The diode 346 can be a Schottky barrier type, such as a HP 5082-2800. The DC output signal generated by the diode 346 is isolated from the resonant circuit 356 of the probe 14 by the capacitor 348. The capacitor 348 typically has a value of 1000 pf.

The isolation amplifier 234 is shown in more detail in FIG. 12. The isolation amplifier 234 is provided with a transistor 358 forming a single stage amplifier operating in the switching mode. The base of the transistor 358 is biased such that the output from the levelling amplifier 310 of the probe drive circuit 218 (FIGS. 9 and 10) drives the transistor 358 between cutoff and saturation, thus producing the standard digital TTL signal appropriate as an input function to the NAND gate 242. The other input to the NAND gate 242 is connected to the timing circuit 214 (FIGS. 9 and 13) via signal path 248. As mentioned previously, the timing circuit 214 outputs a high-level signal over signal path 248 to hold the NAND gate 242 open for the counting period when the standard digital TTL signal generated by the isolation amplifier 234 passes through the NAND gate 242 and is received by the frequency counting circuit 210.

One embodiment of the frequency counting circuit 210 is shown in more detail in FIG. 12. The frequency counting circuit 210 is provided with a frequency divider 360 receiving the standard digital TTL signal via signal path 250. In response thereto, the frequency divider 360 generates a digital signal having a lower frequency than the standard digital TTL signal generated by the isolation amplifier 234 and outputs such digital signal over a signal path 362 to be received as an up count input to a first counter 364. The frequency divider 360 is typically a D-type flip-flop which is configured as a toggle circuit by connecting the low-level active output "Q̄", to the "D" input. Thus, each clock pulse received from the NAND gate 242 causes the frequency divider 360 to switch to the opposite state and thereby divides the standard digital TTL signal output by the isolation amplifier by a factor of 2.

As will be apparent to those skilled in the art, the first counter 364 is daisy chained to a second counter 366 which is daisy chained to a third counter 368, etc. Although only three counters are shown herein, it should be understood that any number of counters can be used. Furthermore, any number of counters having any number of bits may be utilized by the present invention.

The first counter 364, the second counter 366 and the third counter 368 are typically integrated circuits, such as a 74LS193 and have a maximum counting frequency of about 32 MHz. It should be noted that the purpose of the frequency divider 360 is solely to divide the frequency of the standard digital TTL signal generated by the isolation amplifier 234 by 2 because the standard digital TTL signal generated by the isolation amplifier 234 runs faster than the counters can count. Thus, the counters will be counting from a frequency ranging between 12.5 MHz to 25 MHz, which is safely within the counters maximum limit of 32 MHz. If counters are utilized in the present invention that will count faster than 50 MHz, then the frequency divider 360 can be eliminated.

The frequency counting circuit 210 is provided with a latch pulse generator 370 having an "A" input which is connected to the signal path 252. The latch pulse generator 370 is typically a monostable multivibrator, such as a SN74LS221. After the frequency counting circuit 210 has finished counting the standard digital TTL signal, the timing circuit 214 outputs a pulse over signal path 252 to be received by the latch pulse generator 370. In response thereto, the latch pulse generator 370 responds to the negative going edge of the pulse and generates a pulse on both a high-level active output "Q" over a signal path 372 and a low-level active output "$\overline{Q}$" over a signal path 374. The pulse output by the timing circuit 214 also presets the frequency divider 360 via signal path 376.

The high-level active output "Q" of the latch pulse generator 370 clocks a first latch 378 and a second latch 380 to store the final count of the first counter 364, the second counter 366 and the third counter 368. The low-level active output "$\overline{Q}$" of the latch pulse generator 370 is connected to a data ready flag 382 via the signal path 374. The data ready flag is typically a D-type flip-flop such as a SN74LS74. When the low-level active output "$\overline{Q}$" of the latch pulse generator 370 goes low, the data ready flag 382 is reset for toggling the "data ready" line 222 to the ready state and thereby telling the data acquisition system 20 that the digital output signal is ready to be placed onto the signal path 42.

Figure 13:
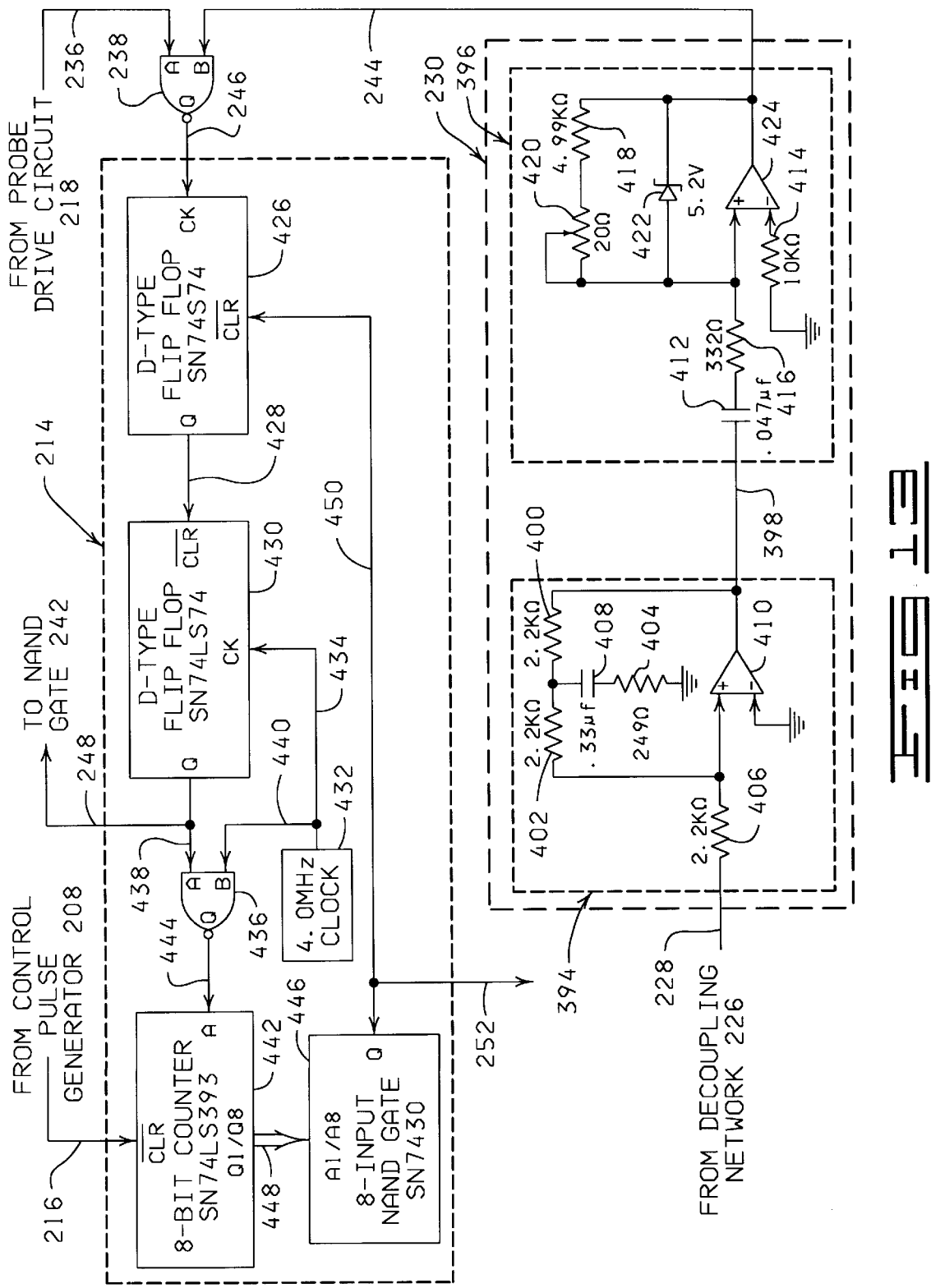
FIG. 13 is a diagrammatic, schematic view illustrating a coincidence detector and a timing circuit of the interrogation circuit of the present invention.

Referring now to FIG. 13, the coincidence detector 230 and the timing circuit 214 will be discussed in more detail. The coincidence detector 230 includes a filter 394 connected to an amplifier differentiator 396 via signal path 398. The filter 394 is provided with a resistor 400, a resistor 402, a resistor 404, a resistor 406, a capacitor 408 and an amplifier 410. The filter 394 has a low static gain so that low frequency fluctuations in the DC output signal of the probe 14, such as the peaking of the parallel resonant circuit 356 of the probe 14, will not be accentuated by the amplifier differentiator 396. However, the instantaneous depression in the level of the DC output signal from the probe 14 due to the implantable sensor 12 loading the probe drive circuit 218 has a much higher frequency content. Therefore, it is desirable to amplify the higher frequencies. The filter 394 has a gain of about 2.0 up to about 350 Hz where the gain of the filter 394 begins increasing linearly with frequency to a gain of approximately 10.0 at 2.0 KHz. Thus, the loading effect of the implantable sensor 12 is accentuated much more than artifacts of the system.

The amplifier differentiator 396 of the coincidence detector 230 is provided with a capacitor 412, a resistor 414, a resistor 416, a resistor 418, a variable resistor 420, a zener diode 422 and an amplifier 424. The amplifier differentiator 396 is an inverting differentiator in that a positive voltage in the output will result from an input voltage with a negative slope. As the frequency of the RF input signal output to the probe 14 approaches very close to the resonant frequency of the implantable sensor 12, the DC output signal begins to diminish. The amplifier differentiator 396 responds to this negative slope by the output going positive, typically to the 5.0 volt limited placed on the output voltage by the zener diode 422. This 5.0 volt signal output by the amplifier differentiator 396 into the NAND gate 238 causes the output of the NAND gate 238 to go to low-level when the other input to the NAND gate 238 is held at high-level via the signal path 236 during the "forward sweep period" of the probe drive circuit 218.

When the frequency of the RF input signal precisely reaches the resonant frequency of the implantable sensor 12, the loading effect is at a maximum and has a slope of zero. At this point, the output of the amplifier differentiator 396 races rapidly negative through the Schmitt trigger level of +1.7 volts causing the output of the NAND gate 238 to return to the high-level.

The output of the NAND gate 238 is connected to a coincidence memory 426, which is typically a D-type flip-flop. The coincidence memory 426 is clocked by the leading edge of the high-level signal output by the NAND gate 238 and in response thereto the coincidence memory 426 generates a signal to be output via a signal path 428 to be received by a pulse delay generator 430 which is typically a D-type flip-flop. The pulse delay generator 430 has a clock input which is connected to an oscillator 432 via a signal path 434. The oscillator is typically a 4.00 MHz crystal oscillator. The output of the pulse delay generator 430 is connected to both an input of the NAND gate 242 (FIG. 12) via signal path 248 and a NAND gate 436 via a signal path 438. It should be noted that the coincidence memory 426 insures that the 63.75 microsecond counting period begins at the leading edge of a clock pulse received from the oscillator 432.

Upon receiving the signal transmitted, by the coincidence memory 426, the clear is removed from the pulse delay generator 430 so that the leading edge of the first clock pulse received by the clock input of the pulse delay generator 430 from the oscillator 432 via signal path 434 causes the output of the pulse delay generator 430 to toggle thereby generating a high-level signal to be transmitted to both the NAND gate 242 and the NAND gate 436.

The signal transmitted to the NAND gate 242 (FIGS. 9 and 12) from the pulse delay generator 430 opens the NAND gate 242 so that the standard digital TTL signal generated by the isolation amplifier 234 is passed through the NAND gate 242 and is received by the frequency counting circuit 210. In response thereto, the frequency counting circuit 210 begins counting the cycles of the standard digital TTL signal.

The signal transmitted from the pulse delay generator 430 is received by the NAND gate 436 via signal path 438 and in response thereto, the NAND gate 436 is opened so that pulses received by the NAND gate 436 from the oscillator 432 via a signal path 440 are passed through the NAND gate 436 to be received by a pulse delay counter 442 via a signal path 444. The output of the pulse delay counter 442 is connected to a NAND gate 446 via a signal path 448. The NAND gate 446 is typically a SN7430 8-bit NAND gate.

When the pulse delay counter 442 receives the pulses passed through the NAND gate 436 via signal path 444, the pulse delay counter 442 counts up to $11111111_{base\ 2}$ or $255_{base\ 10}$, which triggers the output of the NAND gate 446 to go to low-level. In response thereto, the NAND gate 446 outputs the low-level signal over signal path 450 to be received by the coincidence memory 426 and over signal path 252 to be received by the frequency counting circuit 210 (FIGS. 9 and 12). It should be noted that because the oscillator 432 emits a signal of 4.0 MHz, the counting period of the timing circuit is 255×1/4.0 MHz or 63.75 microseconds.

The coincidence memory 426 receives the signal output by the NAND gate 446 and in response thereto, the coincidence memory 426 generates a signal which is transmitted to the pulse delay generator 430 via signal path 428 for clearing the pulse delay generator 430. The pulse delay generator 430 then outputs a low-level signal via signal path 248 to close the NAND gate 242 so that the standard digital TTL signal generated by the isolation amplifier 234 is no longer being passed to the frequency counting circuit 210. In other words, when the NAND gate 446 receives the $11111111_2$ output signal from the pulse delay counter 442, the counting of the standard digital TTL signal output by the isolation amplifier 234 is caused to end.

The data acquisition system 20 will now be discussed in more detail. The data acquisition system 20 provides a collection and storage medium for data study, display and review. In addition, numerical data received by the data acquisition system 20 can be exported to commercially available software, such as Lotus 123, for statistical analysis or to create graphic illustrations.

It should be noted that the resonant frequency of the implantable sensor 12 is typically sampled by the data acquisition system 20 at a 100 Hz data rate. However, the sampled data can be averaged by the data acquisition system 20 in order to filter and compress the sampled data. In addition, the data points displayed and stored by the data acquisition system 20 can represent every point sampled or the average of such sampled data. However, the averaging of the sampled data has inverse effects on wave form resolution.

The data acquisition system 20 can use the following mathematical relationships to model the operation of the implantable sensor 12. The subscript "o" designates a constant that is the value of a variable at the reference pressure (typically 760 mm Hg).

The change in bellows displacement (x) as a function of the pressure deviation (p) from a reference pressure ($P_{pr}$) can be expressed as:

$$x = p/k \tag{1}$$

where the bellows displacement $(x) = d - d_o$, the variable d=capacitance plate separation, the constant $d_o$=capacitance plate separation at the reference pressure ($P_{pr}$), and the constant k=bellows spring constant in units of mm Hg/mm (millimeters of mercury divided by millimeters of travel of the closed lower end plate portion 154 of the bellows 150).

The variable capacitance (C) varies inversely as the variable capacitance plate separation (d) and may be expressed as:

$$C = K/d \tag{2}$$

likewise, $$C_o = K/d_o \tag{3}$$

where the constant K=0.0084 * δ * A, the dielectric constant (δ)=2.7 for silicone fluid, the variable capacitance (C) and the constant capacitance ($C_o$) are in picofarads, the constant capacitance plate area (A) is in square millimeters, and the variable capacitance plate separation (d) and the capacitance plate separation at the pressure reference ($d_o$) are in millimeters.

The variable resonant frequency (f) and the resonant frequency at the reference pressure ($f_o$) of a passive resonant circuit may be expressed as:

$$f = \frac{1}{2\pi\sqrt{LC}} \tag{4}$$

$$f_o = \frac{1}{2\pi\sqrt{LC_o}} \tag{5}$$

where the capacitances (C) and ($C_o$) are in picofarads, the inductance (L) is in microhenries and the resonant frequencies (f) and ($f_o$) are in megahertz.

Equations 2 and 3 may be solved for the variable capacitance plate separation (d) and the capacitance plate separation at the pressure reference ($d_o$)

$$d = K/C \tag{6}$$

$$d_o = K/C_o \tag{7}$$

and, equations 4 and 5 solved for the inverse of the capacitances (C) and ($C_o$)

$$1/C = 4\pi^2 f^2 L \tag{8}$$

$$1/C_o = 4\pi^2 f_o^2 L \tag{9}$$

Equations 1, 6 and 7 can now be combined:

$$\frac{p}{k} = K\left[\frac{1}{C} - \frac{1}{C_o}\right] \tag{10}$$

and, equations 10, 8 and 9 can now be combined:

$$p/k = 4\pi^2 LK[f^2 - f_o^2] \tag{11}$$

Equation 11 can be expressed as:

$$p = 4\pi^2 kKL[f^2 - f_o^2] \tag{12}$$

which can be further simplified as:

$$p = \alpha[f^2 - f_o^2] \tag{13}$$

where, $$\alpha = 4\pi^2 kKL \tag{14}$$

The solution of equation 13 is an ideal solution which assumes no capacitance other than the variable capacitance (C). In reality we must recognize the stray capacitance ($C_s$) which is in no way influenced by pressure but causes the observed resonant frequency (f) to be lower than would be the case without stray capacitance ($C_s$) A frequency correction factor must be applied to both (f) and ($f_o$) to correct for the effect of stray capacitance ($C_s$).

Equation 4 can be rewritten as:

$$f = \frac{1}{2\pi\sqrt{L(C + C_s)}} \tag{15}$$

Solving for $C + C_s$, $$C + C_s = \frac{1}{4\pi^2 f^2 L} \tag{16}$$

Equation 16 can be rewritten as:

$$4\pi^2 f^2 LC + 4\pi^2 f^2 LC_s = 1 \tag{17}$$

The stray capacitance free frequency ($f_i$) can be expressed as:

$$4\pi^2 LC = 1/f_i^2 \tag{18}$$

Equations 17 and 18 can be combined as:

$$\frac{f^2}{f_i^2} = 1 - \frac{f^2}{f_s^2} = 1 - \beta f^2 \tag{19}$$

where ($f_s$) is the resonant frequency that would exist if the only capacitance present was the stray capacitance.

Equation 19 can be solved for the stray capacitance free frequency ($f_i^2$) and expressed as:

$$f_i^2 = \frac{f^2}{1-\beta f^2} \qquad (20)$$

where:

$$\beta = 1/f_s^2 \qquad (21)$$

Because the resonant frequency at the pressure reference ($f_o$) is also effected by stray capacitance ($C_s$), the same correction needs to be applied to the measured value of ($f_o$) to obtain the stray capacitance free value. Therefore, we may write the expression for pressure deviation as:

$$p = \frac{\alpha(f^2 - f_o^2)}{1-\beta f^2} \qquad (22)$$

where (f) and ($f_o$) are now the measured values of frequency with stray capacitance present.

The frequency to pressure relationship of the implantable sensor (equation 22) is a nonlinear second order equation involving three calibration parameters. The calibration factor Alpha ($\alpha$) has been chosen as a sensitivity factor and is primarily determined by the spring constant (k) of the bellows. The standard pressure resonant frequency ($f_o$) is actually a design parameter but is treated as a calibration parameter due to there being some uncertainty in how well it is controlled in fabrication. The calibration parameter beta ($\beta$) is a stray capacitance compensation factor which corrects for loss of sensitivity in the higher pressure region. Equation 22 expresses the pressure deviation (p) in absolute cranial pressure from the pressure reference $P_{pr}$.

Because equation 22 is a second order equation it is completely determined by three points on the equation's curve with each point being defined by a measured frequency at a selected pressure. Theoretically, the three points could be chosen anywhere within the pressure frequency range of the sensor. However, it has been found convenient to use the standard condition point (p=0, f=$f_o$) for the first point, a point well into the positive pressure region for the second point and a point well into the negative pressure region for the third point. The three points can be described as: point 1 (0,$f_o$), point 2 ($p_1$, $f_1$), point 3 ($p_2$, $f_2$).

Equation 22 can now be solved for the sensitivity factor ($\alpha$) and the stray capacitance compensation factor ($\beta$) so as to form a linear equation having two variables:

$$\alpha(f^2-f_o^2)+\beta pf^2=p \qquad (23)$$

The first point (0, $f_o$) is inherently contained in the equation as written thereby requiring only that the other two points be substituted into the equation to form two simultaneous linear equations with two unknowns.

$$\alpha(f_1^2-f_o^2)+\beta p_1 = p_1 \qquad (24)$$

and $$\alpha(f_2^2-f_o^2)+\beta p_2 = p_2 \qquad (25)$$

Equations 24 and 25 can be solved for the sensitivity factor ($\alpha$) and the stray capacitance compensation factor ($\beta$) by methods which are well known in the art.

Once the sensitivity factor ($\alpha$) and the stray capacitance compensation factor ($\beta$) have been determined, equation 22 can be solved for the deviation (p) in absolute cranial pressure about a pressure reference ($P_{pr}$) as a function of the resonant frequency (f) of the implantable sensor. The resonant frequency (f) of the implantable sensor in MegaHertz is determined by multiplying the digital signal output by the counting network by 0.0312.

Once the deviation (p) has been determined, the intracranial pressure ($P_{icp}$) is determined by the formula:

$$P_{icp} = P_{absolute} - P_{atmospheric} \qquad (26)$$

where the atmospheric pressure ($P_{atmospheric}$) can be read from the barometer and ($P_{absolute}$) can be described as:

$$P_{absolute} = p + P_{pr} \qquad (27)$$

where (p) is the deviation from the pressure reference ($P_{pr}$) contained within the implantable sensor. The pressure of the pressure reference ($P_{pr}$) is typically 760 mm Hg (standard pressure)

The formula giving the pressure correction ($P_t$) for body temperature ($T_B$) is as follows:

$$P_t = 1.85 * (T_B - 37) \qquad (28)$$

where the body temperature ($T_B$) is in degrees celsius.

The elements which comprise the implantable sensor have been shown in preferred and sometimes arbitrary shapes which could be modified by one skilled in the art without departing from the teachings of the present invention. It is to be understood that the elements which comprise the implantable sensor may assume any geometric, non-geometric or asymmetrical shape.

The exact dimensions and proportions of the elements described wherein are not essential to the practice of the present invention, but are intended to illustrate the general nature of the embodiments of the present invention. Changes may be made in the embodiments of the invention described herein, or in the parts or the elements of the embodiments described herein, or in the steps or sequence of steps of the methods described herein, without departing from the spirit and/or the scope of the invention as defined in the following claims.

What is claimed is:

1. An apparatus for monitoring the intracranial pressure of a patient, the apparatus comprising:

passive sensor means adapted to be implanted in the skull of a patient for sensing pressure and outputting a signal indicative of the pressure in the patient's skull, the sensor means including an inductor-capacitor circuit having a resonant frequency;

probe means receiving the sensor means output signal when the probe means is positioned near the sensor means for outputting a signal indicative of the pressure sensed by the sensor means; and interrogation circuit means receiving the probe means output signal for automatically outputting a signal proportional to the pressure sensed by the implantable sensor, the interrogation circuit means including:

a probe drive circuit generating an RF signal whose frequency varies in a predetermined manner throughout an operating frequency range encompassing the resonant frequency of the sensor means, the RF signal generated by the probe drive circuit being output to the probe;

a frequency counting circuit means receiving the RF signal generated by the probe drive circuit for selectively counting the number of cycles of the RF signal for a predetermined time;

a coincidence detector means receiving the signal output by the probe means for triggering the frequency counting circuit means to begin counting the number of cycles of the RF signal received by the frequency counting circuit means for a predetermined time, thereby generating the signal proportional to the pressure sensed by the sensor means.

2. The apparatus of claim 1 wherein the probe means and sensor means are adapted to provide:

a maximum energy transfer between the probe means and the inductor-capacitor circuit of the sensor means when the output signal generated by the probe drive circuit corresponds to the resonant frequency of the sensor means, the maximum energy transfer resulting in a minimum value DC voltage being produced in the probe means output signal, thereby denoting the resonant frequency of the implantable sensor; and wherein the coincidence detector means of the interrogation circuit means further comprises a differentiator receiving the probe means output signal, the differentiator differentiating such probe means output signal whereby the differentiator outputs the trigger signal in response to the minimum value DC voltage of the probe means output signal.

3. The apparatus of claim 2 wherein the inductor-capacitor circuit comprises a pressure-sensitive capacitor connected in parallel with an inductor, the inductor-capacitor circuit having a maximum resonant frequency less than 55 MHz.

4. An apparatus for monitoring the intracranial pressure of a patient, the apparatus comprising:

passive sensor means adapted to be implanted in the skull of a patient for sensing pressure and outputting a signal indicative of the pressure in the patient's skull, the sensor means including:

a housing adapted to be disposed within at least a portion of the skull of the patient, the housing defining a chamber;

a pressure sensitive capacitor disposed within the chamber of the housing, the pressure sensitive capacitor comprising:

a first capacitance plate;

a pressure sensitive chamber constructed of a gas impermeable substance, the pressure sensitive chamber defining a gas receiving cavity filled with a gas which forms a pressure reference, a portion of the pressure sensitive chamber defining a second capacitance plate spaced a distance from the first capacitance plate and being movable relative to the first capacitance plate, the pressure sensitive chamber including:

a bellows having an open upper end, a closed lower end plate portion defining the second capacitance plate, an elastomeric sidewall extending generally between the open upper end and the closed lower end plate portion, and an upper flange portion extending a distance outwardly from the sidewall;

coil means electrically connected to a portion of both the pressure sensitive chamber and the first capacitance plate for forming an inductor-capacitor resonant circuit having a resonant frequency, the coil means including an upper end, a lower end and a length extending generally between the upper and lower ends of the coil means, the flange portion and the first capacitance plate being fixed a distance apart less than the length of the coil means;

pressure responsive means for communicating the actual pressure within the cavity in the living entity to the pressure sensitive chamber such that the pressure within the cavity in the living entity opposes the pressure sensitive chamber and varies the distance between the first and second capacitance plates, whereby the resonant frecuency of the inductor-capacitor resonant circuit is varied in response to a chance in pressure sensed by the pressure responsive means;

probe means receiving the sensor means output signal when the probe means is positioned near the sensor means for outputting a signal indicative of the pressure sensed by the sensor means; and interrogation circuit means receiving the probe means output signal for automatically outputting a signal proportional to the pressure sensed by the implantable sensor.

5. The apparatus of claim 4 wherein the coil means further includes a coil form forming a longitudinal bore extending and wherein the pressure sensitive capacitor has an upper end and a lower end, the pressure sensitive capacitor being disposed within the longitudinal bore of the coil form such that the upper end and the lower end of the pressure sensitive capacitor are disposed within the longitudinal bore.

6. The apparatus of claim 5 wherein the coil form of the coil means further includes a shoulder portion extending a distance inwardly into the longitudinal bore of the coil form for maintaining the pressure sensitive capacitor in the longitudinal bore once the pressure sensitive capacitor has been disposed therein.

7. The apparatus of claim 6 wherein the sensor means further includes:

bias means disposed in the longitudinal bore of said coil form for holding the pressure sensitive capacitor in compression, wherein the bias means and the shoulder portion of the coil form cooperate to maintain the pressure sensitive capacitor in the longitudinal bore of said coil form.

8. The apparatus of claim 7 wherein the pressure sensitive capacitor further includes:

a rigid spacer disposed between the upper flange portion of the pressure sensitive chamber and the first capacitance plate, the rigid spacer defining a chamber and being constructed of a non-conductive material, the rigid spacer having first and second opposing ends lying, respectively, in first and second substantially parallel planes; and wherein the bellows further includes a step portion extending outwardly a distance from the sidewall wherein the step portion is configured to be matingly disposed in the chamber of the rigid spacer.

9. The apparatus of claim 6 wherein the upper end of the coil means is attached to a portion of the housing.

10. An apparatus for monitoring the intracranial pressure of a patient, the apparatus comprising:

passive sensor means adapted to be implanted in the skull of a patient for sensing pressure and outputting a signal indicative of the pressure in the patient's skull, the sensor means including:

a housing adapted to be disposed within at least a portion of the skull of the patient, the housing defining a chamber;

a pressure sensitive capacitor disposed within the chamber of the housing, the pressure sensitive capacitor comprising:

a first capacitance plate;

a pressure sensitive chamber constructed of a gas impermeable substance, the pressure sensitive chamber defining a gas receiving cavity filled with a gas which forms a pressure reference, a portion of the pressure sensitive chamber defining a second capacitance plate spaced a distance from the first capacitance plate and being movable relative to the first capacitance plate, the pressure sensitive chamber further including:

an aperture communicating with the gas receiving cavity of the pressure sensitive chamber, the aperture having an upper tapered portion and a lower cylindrical portion; and a tapered pin disposed in the aperture for sealing the pressure reference gas within the gas receiving cavity, the tapered pin having a taper less than the taper of the upper tapered portion of the aperture;

coil means electrically connected to a portion of both the pressure sensitive chamber and the first capacitance plate for forming an inductor-capacitor resonant circuit having a resonant frequency;

pressure responsive means for communicating the actual pressure within the cavity in the living entity to the pressure sensitive chamber such that the pressure within the cavity in the living entity opposes the pressure sensitive chamber and varies the distance between the first and second capacitance plates, whereby the resonant frequency of the inductor-capacitor resonant circuit is varied in response to a change in pressure sensed by the pressure responsive means;

probe means receiving the sensor means output signal when the probe means is positioned near the sensor means for outputting a signal indicative of the pressure sensed by the sensor means; and interrogation circuit means receiving the probe means output signal for automatically outputting a signal proportional to the pressure sensed by the implantable sensor.

11. The apparatus of claim 1 further comprising:

a barometer transmitting a signal indicative of atmospheric pressure; and a data acquisition system means for receiving the signal output by the interrogation circuit means and for receiving the signal transmitted by the barometer, the data acquisition system means automatically computing the intracranial pressure of the patient based on the signals received from the interrogation circuit means and the barometer, whereby the data acquisition system means automatically provides output indications indicative of the intracranial pressure of the patient which are readily understandable by care providers providing care to the patient.

12. The apparatus of claim 11 further comprising:

a visual display means for receiving the output indications output by the data acquisition system means and displaying such output indications.

13. An implantable sensor for sensing pressure within a cavity in a living entity, the implantable sensor comprising:

a housing adapted to be disposed within at least a portion of the cavity in the living entity, the housing defining a chamber;

a pressure sensitive capacitor disposed within the chamber of the housing, the pressure sensitive capacitor comprising:

a first capacitance plate;

a pressure sensitive chamber constructed of a gas impermeable substance, the pressure sensitive chamber defining a gas receiving cavity filled with a gas which forms a pressure reference, a portion of the pressure sensitive chamber defining a second capacitance plate spaced a distance from the first capacitance plate and being movable relative to the first capacitance plate, the pressure sensitive chamber including:

a bellows having an open upper end, a closed lower end Plate portion defining the second capacitance plate, an elastomeric sidewall extending generally between the open upper end and the closed lower end, and an upper flange portion extending a distance outwardly from the sidewall;

coil means electrically connected to a portion of both the pressure sensitive chamber and the first capacitance plate for forming an inductor-capacitor resonant circuit having a resonant frequency, the coil means having an upper end, a lower end and a length extending generally between the upper and lower ends of the coil means, the upper flange portion and the first capacitance Plate being fixed a distance apart less than the length of the coil means;

pressure responsive means for communicating the actual pressure within the cavity in the living entity to the pressure sensitive chamber such that the pressure within the cavity in the living entity opposes the pressure sensitive chamber and varies the distance between the first and second capacitance plates, whereby the resonant frequency of the inductor-capacitor resonant circuit is varied in response to a change in pressure sensed by the pressure responsive means.

14. The implantable sensor of claim 13 wherein the means includes a coil form having a longitudinal bore extending therethrough from the upper end to the lower end of the coil form and wherein the pressure sensitive capacitor has an upper end and a lower end, the pressure sensitive capacitor being such that the upper end and the lower end of the pressure sensitive capacitor are disposed within the longitudinal bore.

15. The implantable sensor of claim 14 wherein the coil form of the coil means includes a shoulder portion extending a distance inwardly into the longitudinal bore of the coil form for maintaining the pressure sensitive capacitor in the longitudinal bore once the pressure sensitive capacitor has been disposed therein.

16. The implantable sensor of claim 15 wherein the implantable sensor further includes:

bias means disposed in the longitudinal bore of the coil form for holding the pressure sensitive capacitor in compression wherein the bias means and the shoulder portion of the coil form cooperate to maintain the pressure sensitive capacitor in the longitudinal bore of the coil form.

17. The implantable sensor of claim 16 wherein the pressure sensitive capacitor further comprises:

a rigid spacer disposed between the upper flange portion of the bellows and the first capacitance plate, the rigid spacer defining a chamber and being constructed of a non-conductive material, the rigid spacer having first and second opposing ends lying, respectively, in first and second substantially parallel planes; and wherein the bellows further comprises a step portion extending outwardly a distance from the sidewall wherein the step portion is configured to be matingly disposed in the chamber of the rigid spacer.

18. The implantable sensor of claim 15 wherein the upper end of the coil form is attached to a portion of the housing.

19. An implantable sensor for sensing pressure within a cavity in a living entity, the implantable sensor comprising:
   a housing adapted to be disposed within at least a portion of the cavity in the living entity, the housing defining a chamber;
   a pressure sensitive capacitor disposed within the chamber of the housing, the pressure sensitive capacitor comprising:
      a first capacitance plate;
      a pressure sensitive chamber constructed of a gas impermeable substance, the pressure sensitive chamber defining a gas receiving cavity filled with a gas which forms a pressure reference, a portion of the pressure sensitive chamber defining a second capacitance plate spaced a distance from the first capacitance plate and being movable relative to the first capacitance plate, the pressure sensitive chamber including:
         an aperture communicating with the gas receiving cavity of the pressure sensitive chamber, the aperture having a tapered upper portion and a cylindrical lower portion;
      coil means electrically connected to a portion of both the pressure sensitive chamber and the first capacitance plate for forming an inductor-capacitor resonant circuit having a resonant frequency;
      pressure responsive means for communicating the actual pressure within the cavity in the living entity to the pressure sensitive chamber such that the pressure within the cavity in the living entity opposes the pressure sensitive chamber and varies the distance between the first and second capacitance plates, whereby the resonant frequency of the inductor-capacitor resonant circuit is varied in response to a change in pressure sensed by the pressure responsive means; and
      a tapered pin disposed in the aperture for sealing the pressure reference gas within the gas receiving cavity wherein the tapered pin has a taper less than the taper of the upper tapered portion of the aperture.

20. A pressure sensitive capacitor comprising:
   a first capacitance plate;
   a pressure sensitive chamber constructed of a gas impermeable substance, the pressure sensitive chamber defining a gas receiving cavity filled with a gas which forms a pressure reference, the pressure sensitive chamber having a portion defining a second capacitance plate spaced a distance from the first capacitance plate and being movable relative to the first capacitance plate wherein the pressure sensitive chamber further defines:
      an aperture communicating with the gas receiving cavity of the pressure sensitive chamber, the aperture having an upper tapered portion and a lower cylindrical portion;
      a tapered pin disposed in the aperture for sealing the pressure reference gas within the gas receiving cavity wherein the tapered Pin has a taper less than the taper of the upper tapered portion of the aperture; and
   wherein actual pressure surrounding the pressure sensitive chamber opposes the pressure sensitive chamber and varies the distance between the first and second capacitance plates, whereby the capacitance of the pressure sensitive capacitor is varied based on the actual pressure surrounding the pressure sensitive chamber.

21. An interrogation circuit for outputting RF signals to a probe which is electrically coupled to an implantable sensor having a resonant frequency and being implanted in a cavity within a patient, the interrogation circuit comprising:
   a probe drive circuit means for generating RF signals whose frequency varies in a predetermined manner throughout an operating frequency range, the RF signals generated by the probe drive circuit means being output to the probe;
   a frequency counting circuit means receiving the RF signal output by the probe drive circuit means for selectively counting the number of cycles of the RF signal for a predetermined time; and
   a coincidence detector means for receiving a signal output by the probe, the signal output by the probe being indicative of the pressure sensed by the implantable sensor and the coincidence detector means outputting a trigger signal to be received by the frequency counting circuit means for triggering the frequency counting circuit means to begin counting the number of cycles of the RF signal output by the probe drive circuit means for a predetermined time so as to generate a signal proportional to the pressure sensed by the implantable sensor.

22. The interrogation circuit of claim 21 wherein the frequency counting circuit means and coincidence detector means are adapted to provide a maximum energy transfer between the probe and the implantable sensor when the output signal generated by the probe drive circuit means corresponds to the resonant frequency of the implantable sensor, the maximum energy transfer resulting in a minimum value DC voltage being produced in the probe output signal thereby denoting the resonant frequency of the implantable sensor; and
   wherein the coincidence detector means further includes a differentiator receiving the probe output signal, the differentiator differentiating such probe output signal whereby the differentiator outputs the trigger signal in response to the minimum value DC voltage of the probe output signal.

23. A method for forming an implantable sensor for sensing the pressure within a cavity within a living entity, the method comprising the steps of:
   disposing an implantable sensor and a quantity of fluid within a sealed container, the implantable sensor having a housing defining a chamber and the implantable sensor having a pressure reference disposed within the chamber of the housing;
   drawing a vacuum within the sealed container;
   submerging the implantable sensor within the quantity of fluid;
   releasing the vacuum in the sealed container back to atmospheric pressure for allowing a quantity of fluid to migrate into the implantable sensor through an aperture formed through the housing of the implantable sensor;
   exchanging the quantity of fluid within the implantable sensor with a quantity of fluid substantially saturated with gas at a temperature substantially equal to standard body temperature; and
   sealing the implantable sensor, whereby the implantable sensor has a calibration baseline that remains substantially constant throughout the life of the implantable sensor.

24. The method of claim 23 wherein the step of exchanging the quantity of fluid within the implantable sensor is further defined as:

injecting a quantity of fluid saturated with gas at a temperature substantially equal to standard body temperature while maintaining the implantable sensor at standard body temperature.

25. An apparatus for monitoring the intracranial pressure of a patient, the apparatus comprising:

passive sensor means adapted to be implanted in the skull of a patient for sensing pressure and outputting a signal indicative of the pressure in the patient's skull, the sensor means including:
- a housing adapted to be disposed within at least a portion of the skull of the patient, the housing defining a chamber;
- a pressure sensitive capacitor disposed within the chamber of the housing, the pressure sensitive capacitor comprising:
  - a first capacitance plate; and
  - a pressure sensitive chamber constructed of a gas impermeable substance, the pressure sensitive chamber defining a gas receiving cavity filled with a gas which forms a pressure reference, a portion of the pressure sensitive chamber defining a second capacitance plate spaced a distance from the first capacitance plate and being movable relative to the first capacitance plate;
- coil means electrically connected to a portion of both the pressure sensitive chamber and the first capacitance plate for forming an inductor-capacitor resonant circuit having a resonant frequency;
- pressure responsive means for communicating the actual pressure within the cavity in the living entity to the pressure sensitive chamber such that the pressure within the cavity in the living entity opposes the pressure sensitive chamber and varies the distance between the first and second capacitance plates, whereby the resonant frequency of the inductor-capacitor resonant circuit is varied in response to a change in pressure sensed by the pressure responsive means, the pressure responsive means of the sensor means including:
  - a flexible membrane connected to a portion of the housing such that the flexible membrane communicates with the chamber formed in the housing whereby the flexible membrane communicates the cranial pressure to the chamber of the housing;
  - a quantity of fluid disposed within the housing of the sensor means, the fluid serving to transmit deformations of the flexible membrane into compression of the pressure sensitive chamber, wherein the fluid is substantially saturated with gas at a temperature substantially equal to standard body temperature;

probe means receiving the sensor means output signal when the probe means is positioned near the sensor means for outputting a signal indicative of the pressure sensed by the sensor means; and interrogation circuit means receiving the probe means output signal for automatically outputting a signal proportional to the pressure sensed by the implantable sensor.

26. An apparatus for monitoring the intracranial pressure of a patient, the apparatus comprising:

passive sensor means adapted to be implanted in the skull of a patient for sensing pressure and outputting a signal indicative of the pressure in the patient's skull, the sensor means including:
- a housing adapted to be disposed within at least a portion of the skull of the patient, the housing defining a chamber;
- a pressure sensitive capacitor disposed within the chamber of the housing, the pressure sensitive capacitor comprising:
  - a first capacitance plate;
  - a pressure sensitive chamber constructed of a gas impermeable substance, the pressure sensitive chamber defining a gas receiving cavity filled with a gas which forms a pressure reference, a portion of the pressure sensitive chamber defining a second capacitance plate spaced a distance from the first capacitance plate and being movable relative to the first capacitance plate, the pressure sensitive chamber including:
    - a bellows having a sidewall constructed of alternating layers of a first metal and a second metal wherein the sidewall has at least 3 layers of the first metal and at least 2 layers of the second metal;
  - coil means electrically connected to a portion of both the pressure sensitive chamber and the first capacitance plate for forming an inductor-capacitor resonant circuit having a resonant frequency;
  - pressure responsive means for communicating the actual pressure within the cavity in the living entity to the pressure sensitive chamber such that the pressure within the cavity in the living entity opposes the pressure sensitive chamber and varies the distance between the first and second capacitance plates, whereby the resonant frequency of the inductor-capacitor resonant circuit is varied in response to a change in pressure sensed by the pressure responsive means;

probe means receiving the sensor means output signal when the probe means is positioned near the sensor means for outputting a signal indicative of the pressure sensed by the sensor means; and interrogation circuit means receiving the probe means output signal for automatically outputting a signal proportional to the pressure sensed by the implantable sensor.

27. The apparatus of claim 26 wherein the first metal is nickel and the second metal is copper.

28. An implantable sensor for sensing pressure within a cavity in a living entity, the implantable sensor comprising:

a housing adapted to be disposed within at least a portion of the cavity in the living entity, the housing defining a chamber;

a pressure sensitive capacitor disposed within the chamber of the housing, the pressure sensitive capacitor comprising:
- a first capacitance plate;
- a pressure sensitive chamber constructed of a gas impermeable substance, the pressure sensitive chamber defining a gas receiving cavity filled with a gas which forms a pressure reference, a portion of the pressure sensitive chamber defining a second capacitance plate spaced a distance from the first capacitance plate and being movable relative to the first capacitance plate;
- coil means electrically connected to a portion of both the pressure sensitive chamber and the first capacitance plate for forming an inductor-capacitor resonant circuit having a resonant frequency;

pressure responsive means for communicating the actual pressure within the cavity in the living entity to the pressure sensitive chamber such that the pressure within the cavity in the living entity opposes the pressure sensitive chamber and varies the distance between the first and second capacitance plates, whereby the resonant frequency of the inductor-capacitor resonant circuit is varied in response to a change in pressure sensed by the pressure responsive means, the pressure responsive means including:

a flexible membrane connected to a portion of the housing such that the flexible membrane communicates with the chamber formed in the housing wherein the flexible membrane communicates the cranial pressure to the chamber of the housing; and a quantity of fluid disposed within the housing of the implantable sensor, the fluid serving to transmit deformations of the flexible membrane into compression of the bellows wherein the fluid is substantially saturated with gas at a temperature substantially equal to standard body temperature.

29. An implantable sensor for sensing pressure within a cavity in a living entity, the implantable sensor comprising:

a housing adapted to be disposed within at least a portion of the cavity in the living entity, the housing defining a chamber;

a pressure sensitive capacitor disposed within the chamber of the housing, the pressure sensitive capacitor comprising:

a first capacitance plate;

a pressure sensitive chamber constructed of a gas impermeable substance, the pressure sensitive chamber defining a gas receiving cavity filled with a gas which forms a pressure reference, a portion of the pressure sensitive chamber defining a second capacitance plate spaced a distance from the first capacitance plate and being movable relative to the first capacitance plate, the pressure sensitive chamber including:

a bellows having a sidewall constructed of alternating layers of a first metal and a second metal wherein the sidewall has at least 3 layers of the first metal and at least 2 layers of the second metal;

coil means electrically connected to a portion of both the pressure sensitive chamber and the first capacitance plate for forming an inductor-capacitor resonant circuit having a resonant frequency;

pressure responsive means for communicating the actual pressure within the cavity in the living entity to the pressure sensitive chamber such that the pressure within the cavity in the living entity opposes the pressure sensitive chamber and varies the distance between the first and second capacitance plates, whereby the resonant frequency of the inductor-capacitor resonant circuit is varied in response to a change in pressure sensed by the pressure responsive means.

30. The implantable sensor of claim 29 wherein the first metal is nickel and the second metal is copper.

31. A pressure sensitive capacitor comprising:

a first capacitance plate;

a pressure sensitive chamber constructed of a gas impermeable substance, the pressure sensitive chamber defining a gas receiving cavity filled with a gas which forms a pressure reference, the pressure sensitive chamber having a portion defining a second capacitance plate spaced a distance from the first capacitance plate and being movable relative to the first capacitance plate, wherein the pressure sensitive chamber further comprises:

a bellows having a sidewall constructed of alternating layers of a first metal and a second metal wherein the sidewall has at least 3 layers of the first metal and at least 2 layers of the second metal; and wherein actual pressure surrounding the pressure sensitive chamber opposes the pressure sensitive chamber and varies the distance between the first and second capacitance plates, whereby the capacitance of the pressure sensitive capacitor is varied based on the actual pressure surrounding the pressure sensitive chamber.

32. The pressure sensitive capacitor of claim 31 wherein the first metal is nickel and the second metal is copper.

33. An apparatus for monitoring the intracranial pressure of a patient, the apparatus comprising:

passive sensor means adapted to be implanted in the skull of a patient for sensing pressure and outputting a signal indicative of the pressure in the patient's skull, the sensor means including an inductor-capacitor circuit having a resonant frequency;

probe means receiving the sensor means output signal when the probe means is positioned near the sensor means for outputting a signal indicative of the pressure sensed by the sensor means; and interrogation circuit means receiving the probe means output signal for automatically outputting a signal relative to the pressure sensed by the implantable sensor, the interrogation circuit means including:

a probe drive circuit generating an RF signal whose frequency varies in a predetermined manner throughout an operating frequency range encompassing the resonant frequency of the sensor means, the RF signal generated by the probe drive circuit being output to the probe;

a frequency counting circuit means receiving the RF signal generated by the probe drive circuit for selectively counting the number of cycles of the RF signal for a predetermined time;

a coincidence detector means receiving the signal output by the probe means for triggering the frequency counting circuit means to begin counting the number of cycles of the RF signal received by the frequency counting circuit means for a predetermined time, thereby generating the signal relative to the pressure sensed by the sensor means.

34. An interrogation circuit for outputting RF signals to a probe which is electrically coupled to an implantable sensor having a resonant frequency and being implanted in a cavity within a patient, the interrogation circuit comprising:

a probe drive circuit means for generating RF signals whose frequency varies in a predetermined manner throughout an operating frequency range, the RF signals generated by the probe drive circuit means being output to the probe;

a frequency counting circuit means receiving the RF signal output by the probe drive circuit means for selectively counting the number of cycles of the RF signal for a predetermined time; and a coincidence detector means for receiving a signal output by the probe, the signal output by the probe being indicative of the pressure sensed by the implantable sensor and the coincidence detector means outputting a trigger signal to be received by the frequency counting circuit means for triggering the frequency counting circuit means to begin counting the number of cycles of the RF signal output by the probe drive circuit means for a predetermined time so as to generate a signal relative to the pressure sensed by the implantable sensor.

* * * * *